(12) United States Patent
Yoo et al.

(10) Patent No.: US 11,696,495 B2
(45) Date of Patent: Jul. 4, 2023

(54) ORGANIC EMITTING COMPOUND, AND ORGANIC LIGHT EMITTING DIODE AND ORGANIC LIGHT EMITTING DISPLAY DEVICE INCLUDING THE SAME

(71) Applicant: LG Display Co., Ltd., Seoul (KR)

(72) Inventors: Mi-Sang Yoo, Paju-si (KR); Jeong-Eun Baek, Paju-si (KR); Joong-Hwan Yang, Paju-si (KR); Bo-Min Seo, Paju-si (KR)

(73) Assignee: LG Display Co., Ltd., Seoul (KR)

( * ) Notice: Subject to any disclaimer, the term of this patent is extended or adjusted under 35 U.S.C. 154(b) by 612 days.

(21) Appl. No.: 16/526,523

(22) Filed: Jul. 30, 2019

(65) Prior Publication Data

US 2020/0044157 A1 Feb. 6, 2020

(30) Foreign Application Priority Data

Aug. 6, 2018 (KR) ........................ 10-2018-0091234

(51) Int. Cl.
*H01L 51/50* (2006.01)
*H10K 85/60* (2023.01)
(Continued)

(52) U.S. Cl.
CPC ......... *H10K 85/623* (2023.02); *C07C 255/50* (2013.01); *C09K 11/06* (2013.01);
(Continued)

(58) Field of Classification Search
None
See application file for complete search history.

(56) References Cited

U.S. PATENT DOCUMENTS 9,120,748 B2 9/2015 Takashima et al.
9,512,137 B2 12/2016 Ito et al.
(Continued)

FOREIGN PATENT DOCUMENTS

CN 101617417 A 12/2009
CN 102576814 A 7/2012
(Continued)

OTHER PUBLICATIONS

Taiwan Intellectual Property Office, Office Action, TW Patent Application No. 108127185, dated Feb. 18, 2020, seven pages (with concise explanation of relevance).
(Continued)

*Primary Examiner* — Gregory D Clark
(74) *Attorney, Agent, or Firm* — Fenwick & West LLP

(57) ABSTRACT

The present disclosure provides an organic emitting compound of the following Formula, and an organic light emitting diode, which includes a first electrode; a second electrode facing the first electrode; and a first emitting material layer positioned between the first electrode and the second electrode and including a first host and the organic emitting compound, and an organic light emitting display device including the organic light emitting diode.

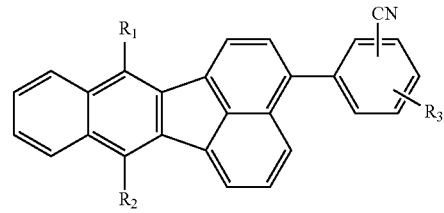

20 Claims, 4 Drawing Sheets

(51) Int. Cl.
*C09K 11/06* (2006.01)
*C07C 255/50* (2006.01)
*H10K 50/11* (2023.01)
*H10K 50/18* (2023.01)
*H10K 59/12* (2023.01)
*H10K 101/10* (2023.01)
*H10K 101/30* (2023.01)
*H10K 101/40* (2023.01)

(52) U.S. Cl.
CPC .. *C07C 2603/52* (2017.05); *C09K 2211/1007* (2013.01); *C09K 2211/1011* (2013.01); *H10K 50/11* (2023.02); *H10K 50/18* (2023.02); *H10K 59/12* (2023.02); *H10K 2101/10* (2023.02); *H10K 2101/30* (2023.02); *H10K 2101/40* (2023.02)

(56) References Cited

U.S. PATENT DOCUMENTS

| | | | |
|---|---|---|---|
| 2007/0012915 A1* | 1/2007 | Lee | H01L 51/5012 257/40 |
| 2009/0015144 A1 | 1/2009 | Takashima et al. | |
| 2010/0039027 A1* | 2/2010 | Takashima | C07D 235/18 548/310.7 |
| 2012/0256172 A1* | 10/2012 | Ito | C07D 493/04 257/E51.026 |
| 2016/0104847 A1 | 4/2016 | Xia et al. | |
| 2016/0149139 A1 | 5/2016 | Xia et al. | |

FOREIGN PATENT DOCUMENTS

| | | | |
|---|---|---|---|
| CN | 104629729 A | 5/2015 | |
| CN | 107382749 A | 11/2017 | |
| EP | 2 113 954 A1 | 11/2009 | |
| JP | 2014-096572 A | 5/2014 | |
| JP | 2015-204357 | * 11/2015 | ............ H01L 51/50 |
| JP | 2015-204357 A | 11/2015 | |
| KR | 10-1622192 B1 | 12/2015 | |
| TW | I432553 B | 4/2014 | |
| WO | WO 2016/133058 A1 | 8/2016 | |
| WO | WO 2017/104767 A1 | 6/2017 | |

OTHER PUBLICATIONS

European Patent Office, European Search Report, EP Patent Application No. 19189867, dated Dec. 5, 2019, one page.
First Office Action and Search Report, State Intellectual Property Office of People's Republic of China Patent Application No. 201910698990.3, dated Mar. 2, 2022, 17 pages.

* cited by examiner

ORGANIC EMITTING COMPOUND, AND ORGANIC LIGHT EMITTING DIODE AND ORGANIC LIGHT EMITTING DISPLAY DEVICE INCLUDING THE SAME

CROSS-REFERENCE TO RELATED APPLICATIONS

The present application claims the benefit of Republic of Korea Patent Application No. 10-2018-0091234 filed in the Republic of Korea on Aug. 6, 2018, which is hereby incorporated by reference in its entirety.

BACKGROUND

Field of Technology

The present disclosure relates to an organic emitting compound, and more particularly, to an organic emitting compound including a benzofluoranthene core and an organic light emitting diode and an organic light emitting display device including the same.

Discussion of the Related Art

Recently, requirement for flat panel display devices having small occupied area is increased. Among the flat panel display devices, a technology of an organic light emitting display device including an organic light emitting diode (OLED) is rapidly developed.

The OLED emits light by injecting electrons from a cathode as an electron injection electrode and holes from an anode as a hole injection electrode into an emitting layer, combining the electrons with the holes, generating an exciton, and transforming the exciton from an excited state to a ground state. A flexible transparent substrate, for example, a plastic substrate, can be used as a base substrate where elements are formed. In addition, the emitting diode can be operated at a voltage (e.g., 10V or below) lower than a voltage required to operate other display devices and has low power consumption. Moreover, the light from the emitting diode has excellent color purity.

The OLED includes a first electrode as the anode, a second electrode as the cathode being spaced apart from the first electrode and an organic emitting layer therebetween.

The organic emitting layer may have a single-layered structure of an emitting material layer (EML). Alternatively, to improve the emission efficiency, the organic emitting layer may have a multi-layered structure. For example, the organic emitting layer may include a hole injection layer (HIL), a hole transporting layer (HTL), the EML, an electron transporting layer (ETL) and an electron injection layer (EIL).

The hole is provided from the first electrode as the anode into the EML through the HIL and the HTL, and the electron is provided from the second electrode as the cathode into the EML through the EIL and the ETL. The hole and the electron are combined in the EML to generate an exciton, and the exciton is transformed from an excited state to a ground state such that the light is emitted from the organic emitting layer.

The emitting material for the EML may be classified into a fluorescent material and a phosphorescent material.

In the fluorescent material, since only singlet exciton is involved in emission, the fluorescent material provides low emitting efficiency (quantum efficiency).

In the phosphorescent material, since not only singlet exciton but also triplet exciton is involved in emission, the phosphorescent material provides high emitting efficiency. However, since the phosphorescent material requires rare metal atom, e.g., Ir, the phosphorescent material is very expensive. In addition, there is a limitation of blue emission.

SUMMARY

The present disclosure is directed to an organic compound and an OLED and an organic light emitting display device including the same that substantially obviate one or more of the problems associated with the limitations and disadvantages of the related conventional art.

Additional features and advantages of the present disclosure are set forth in the description which follows, and will be apparent from the description, or evident by practice of the present disclosure. The objectives and other advantages of the present disclosure are realized and attained by the features described herein as well as in the appended drawings.

To achieve these and other advantages in accordance with the purpose of the embodiments of the present disclosure, as described herein, an organic emitting compound of Formula:

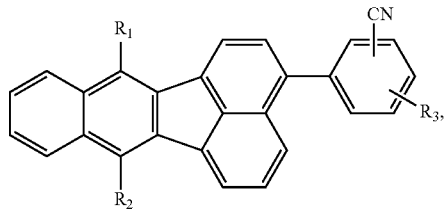

wherein each of $R_1$, $R_2$ and $R_3$ is independently selected from the group consisting of hydrogen, C1 to C20 alkyl group, C1 to C20 alkoxy group, C1 to C20 silyl group, C6 to C30 aryl group, C5 to C30 heteroaryl group and amine group.

Another aspect of the present disclosure is an organic light emitting diode comprising: a first electrode; a second electrode facing the first electrode; and a first emitting material layer positioned between the first and second electrodes and including a first host and an organic emitting compound, wherein the organic emitting compound is represent by Formula:

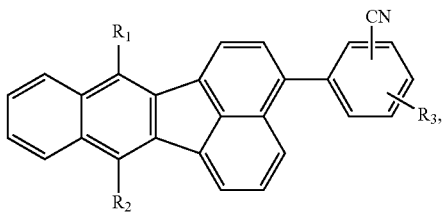

wherein each of $R_1$, $R_2$ and $R_3$ is independently selected from the group consisting of hydrogen, C1 to C20 alkyl group, C1 to C20 alkoxy group, C1 to C20 silyl group, C6 to C30 aryl group, C5 to C30 heteroaryl group and amine group.

Another aspect of the present disclosure is an organic light emitting display device comprising: a substrate; an organic light emitting diode on the substrate, the organic light emitting diode including: a first electrode; a second electrode facing the first electrode; and a first emitting material layer positioned between the first and second electrodes and including a first host and an organic emitting compound; and an encapsulation film covering the organic light emitting diode, wherein the organic emitting compound is represent by Formula:

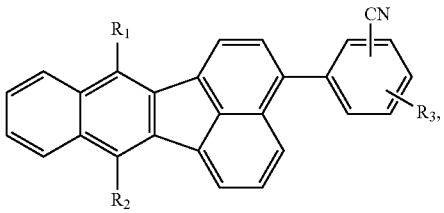

wherein each of $R_1$, $R_2$ and $R_3$ is independently selected from the group consisting of hydrogen, C1 to C20 alkyl group, C1 to C20 alkoxy group, C1 to C20 silyl group, C6 to C30 aryl group, C5 to C30 heteroaryl group and amine group.

It is to be understood that both the foregoing general description and the following detailed description are exemplary and explanatory and are intended to further explain the present disclosure as claimed.

BRIEF DESCRIPTION OF THE DRAWINGS

The accompanying drawings, which are included to provide a further understanding of the present disclosure and are incorporated in and constitute a part of this specification, illustrate embodiments of the present disclosure and together with the description serve to explain the principles of the present disclosure.

DETAILED DESCRIPTION

Reference will now be made in detail to some of the examples and preferred embodiments, which are illustrated in the accompanying drawings.

Figure 1:
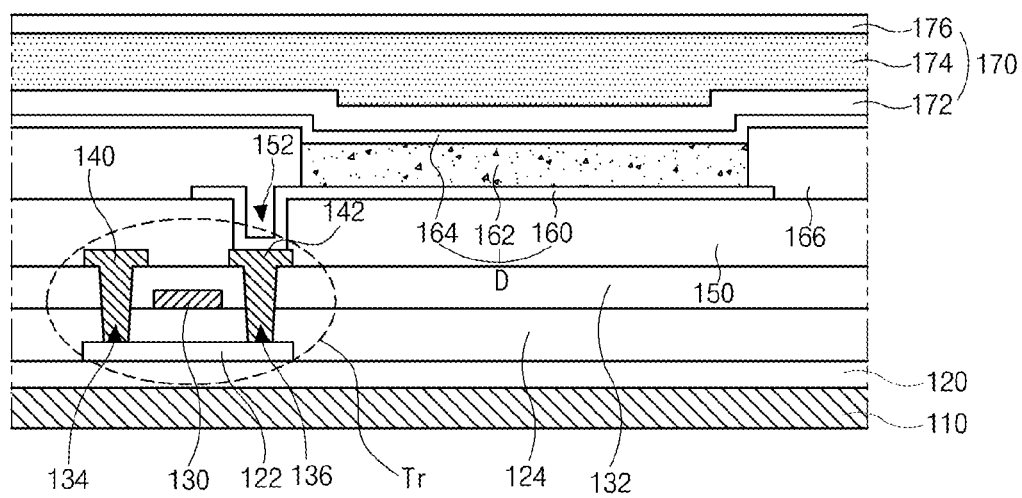
FIG. 1 is a schematic cross-sectional view of an organic light emitting display device of the present disclosure.

FIG. 1 is a schematic cross-sectional view of an organic light emitting display device of the present disclosure.

As shown in FIG. 1, the organic light emitting display device 100 includes a substrate 110, a TFT Tr and an OLED D connected to the TFT Tr.

The substrate 110 may be a glass substrate or a plastic substrate. For example, the substrate 110 may be a polyimide substrate.

A buffer layer 120 is formed on the substrate, and the TFT Tr is formed on the buffer layer 120. The buffer layer 120 may be omitted.

A semiconductor layer 122 is formed on the buffer layer 120. The semiconductor layer 122 may include an oxide semiconductor material or polycrystalline silicon.

When the semiconductor layer 122 includes the oxide semiconductor material, a light-shielding pattern (not shown) may be formed under the semiconductor layer 122. The light to the semiconductor layer 122 is shielded or blocked by the light-shielding pattern such that thermal degradation of the semiconductor layer 122 can be prevented. On the other hand, when the semiconductor layer 122 includes polycrystalline silicon, impurities may be doped into both sides of the semiconductor layer 122.

A gate insulating layer 124 is formed on the semiconductor layer 122. The gate insulating layer 124 may be formed of an inorganic insulating material such as silicon oxide or silicon nitride.

A gate electrode 130, which is formed of a conductive material, e.g., metal, is formed on the gate insulating layer 124 to correspond to a center of the semiconductor layer 122.

In FIG. 1, the gate insulating layer 124 is formed on an entire surface of the substrate 110. Alternatively, the gate insulating layer 124 may be patterned to have the same shape as the gate electrode 130.

An interlayer insulating layer 132, which is formed of an insulating material, is formed on the gate electrode 130. The interlayer insulating layer 132 may be formed of an inorganic insulating material, e.g., silicon oxide or silicon nitride, or an organic insulating material, e.g., benzocyclobutene or photo-acryl.

The interlayer insulating layer 132 includes first and second contact holes 134 and 136 exposing both sides of the semiconductor layer 122. The first and second contact holes 134 and 136 are positioned at both sides of the gate electrode 130 to be spaced apart from the gate electrode 130.

The first and second contact holes 134 and 136 are formed through the gate insulating layer 124. Alternatively, when the gate insulating layer 124 is patterned to have the same shape as the gate electrode 130, the first and second contact holes 134 and 136 is formed only through the interlayer insulating layer 132.

A source electrode 140 and a drain electrode 142, which are formed of a conductive material, e.g., metal, are formed on the interlayer insulating layer 132.

The source electrode 140 and the drain electrode 142 are spaced apart from each other with respect to the gate electrode 130 and respectively contact both sides of the semiconductor layer 122 through the first and second contact holes 134 and 136.

The semiconductor layer 122, the gate electrode 130, the source electrode 140 and the drain electrode 142 constitute the TFT Tr. The TFT Tr serves as a driving element.

In the TFT Tr, the gate electrode 130, the source electrode 140, and the drain electrode 142 are positioned over the semiconductor layer 122. Namely, the TFT Tr has a coplanar structure.

Alternatively, in the TFT Tr, the gate electrode may be positioned under the semiconductor layer, and the source and drain electrodes may be positioned over the semiconductor layer such that the TFT Tr may have an inverted staggered structure. In this instance, the semiconductor layer may include amorphous silicon.

Although not shown, the gate line and the data line cross each other to define the pixel region, and the switching TFT is formed to be connected to the gate and data lines. The switching TFT is connected to the TFT Tr as the driving element.

In addition, the power line, which may be formed to be parallel to and spaced apart from one of the gate and data lines, and the storage capacitor for maintaining the voltage of the gate electrode of the TFT Tr in one frame may be further formed.

A passivation layer 150, which includes a drain contact hole 152 exposing the drain electrode 142 of the TFT Tr, is formed to cover the TFT Tr.

A first electrode 160, which is connected to the drain electrode 142 of the TFT Tr through the drain contact hole 152, is separately formed in each pixel region. The first electrode 160 may be an anode and may be formed of a conductive material having a relatively high work function. For example, the first electrode 160 may be formed of a transparent conductive material such as indium-tin-oxide (ITO) or indium-zinc-oxide (IZO).

When the OLED device 100 is operated in a top-emission type, a reflection electrode or a reflection layer may be formed under the first electrode 160. For example, the reflection electrode or the reflection layer may be formed of aluminum-palladium-copper (APC) alloy.

A bank layer 166 is formed on the passivation layer 150 to cover an edge of the first electrode 160. Namely, the bank layer 166 is positioned at a boundary of the pixel region and exposes a center of the first electrode 160 in the pixel region.

An organic emitting layer 162 is formed on the first electrode 160. The organic emitting layer 162 includes an organic emitting compound of the present disclosure. The organic emitting compound may be used as a dopant, and the organic emitting layer 162 may further include a host. For example, the dopant may be doped with a ratio of approximately 1 to 30 wt % with respect to the host. In addition, the organic emitting layer 162 may further include a delayed fluorescent compound as another dopant. In this instance, a summation of the organic emitting compound and the delayed fluorescent compound may have a range of approximately 1 to 50 wt % with respect to the host. In one instance, the organic emitting layer 162 emits blue light.

The organic emitting layer 162 may have a single-layered structure of an emitting material layer including the organic emitting compound. To increase an emitting efficiency of the OLED device, the organic emitting layer 162 may have a multi-layered structure.

A second electrode 164 is formed over the substrate 110 where the organic emitting layer 162 is formed. The second electrode 164 covers an entire surface of the display area and may be formed of a conductive material having a relatively low work function to serve as a cathode. For example, the second electrode 164 may be formed of aluminum (Al), magnesium (Mg) or Al—Mg alloy.

The first electrode 160, the organic emitting layer 162, and the second electrode 164 may constitute the OLED D.

An encapsulation film 170 is formed on the second electrode 164 to prevent penetration of moisture into the OLED D. The encapsulation film 170 includes a first inorganic insulating layer 172, an organic insulating layer 174, and a second inorganic insulating layer 176 sequentially stacked together, but it is not limited thereto.

A polarization plate (not shown) for reducing an ambient light reflection may be disposed over the top-emission type OLED D. For example, the polarization plate may be a circular polarization plate.

In addition, a cover window (not shown) may be attached to the encapsulation film 170 or the polarization plate. In this instance, the substrate 110 and the cover window have a flexible property such that a flexible display device may be provided.

Figure 2:
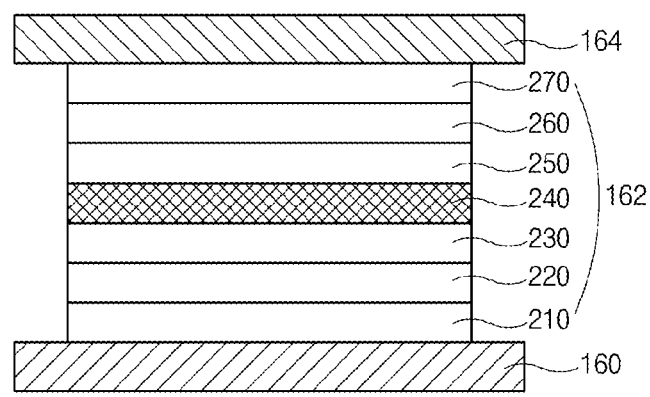
FIG. 2 is a schematic-cross sectional view of an OLED according to a first embodiment of the present disclosure.

FIG. 2 is a schematic-cross sectional view of an OLED according to a first embodiment of the present disclosure.

As shown in FIG. 2, the OLED D includes the first electrode 160 and the second electrode 164, which face each other, and the organic emitting layer 162 therebetween. The organic emitting layer 162 includes an emitting material layer (EML) 240 between the first and second electrodes 160 and 164, a hole transporting layer (HTL) 220 between the first electrode 160 and the EML 240 and an electron transporting layer (ETL) 260 between the second electrode 164 and the EML 240.

In addition, the organic emitting layer 162 may further include a hole injection layer (HIL) 210 between the first electrode 160 and the HTL 220 and an electron injection layer (EIL) 270 between the second electrode 164 and the ETL 260.

Moreover, the organic emitting layer 162 may further include an electron blocking layer (EBL) 230 between the HTL 220 and the EML 240 and a hole blocking layer (HBL) 250 between the EML 240 and the ETL 260.

The organic emitting layer 162, preferably the EML 240 includes an organic emitting compound of Formula 1 as a dopant.

[Formula 1]

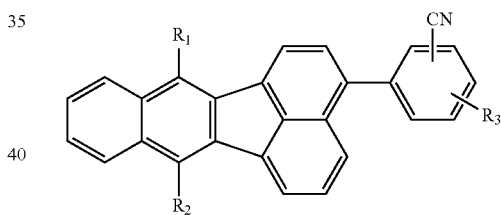

In Formula 1, each of $R_1$, $R_2$ and $R_3$ is independently selected from the group consisting of hydrogen, C1 to C20 alkyl group, C1 to C20 alkoxy group, C1 to C20 silyl group, C6 to C30 aryl group, C5 to C30 heteroaryl group and amine group. For example, each of $R_1$, $R_2$ and $R_3$ may be independently selected from the group consisting of phenyl, naphthyl and anthracenyl.

Namely, the organic emitting compound of the present disclosure includes a benzofluoranthene core and a cyanophenylene moiety bonded (connected) to the benzofluoranthene core. In this instance, the cyanophenylene moiety is directly bonded to the benzofluoranthene core.

The organic emitting compound has a fluorescent emission property and narrow full width at half maximum (FWHM). In addition, since the cyanophenylene moiety is directly bonded to the benzofluoranthene core, the organic emitting compound has a deep HOMO level.

For example, the organic emitting compound may be selected from materials in Formula 2.

[Formula 2]
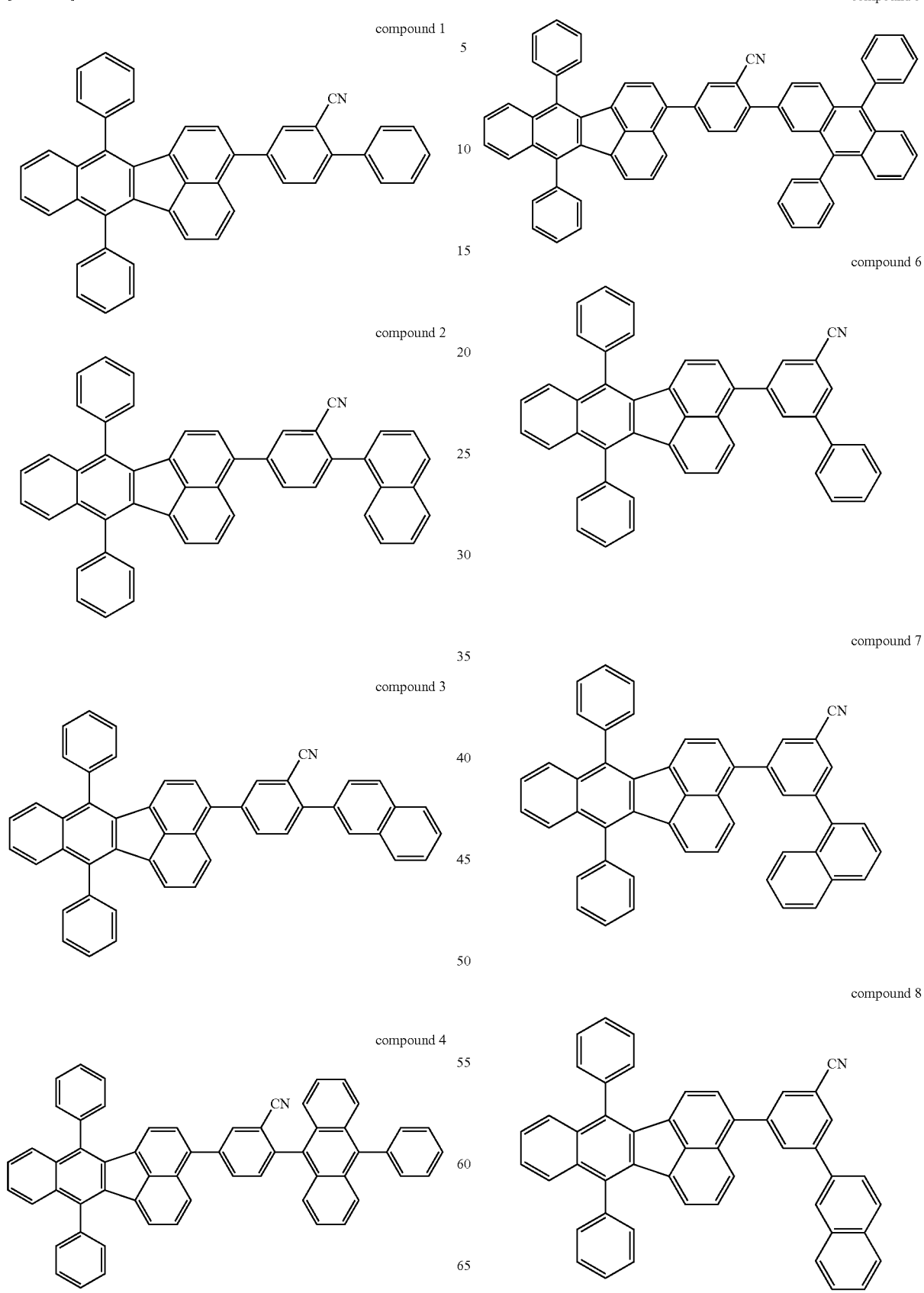

compound 9
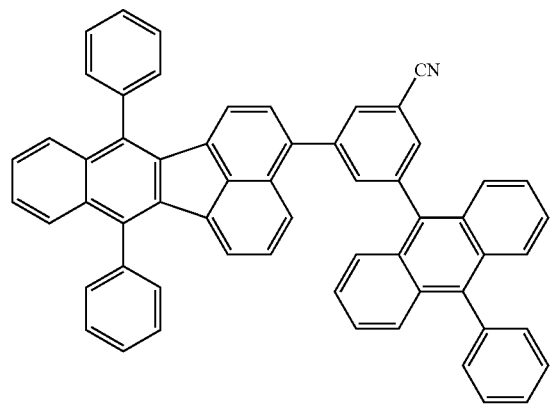
compound 10
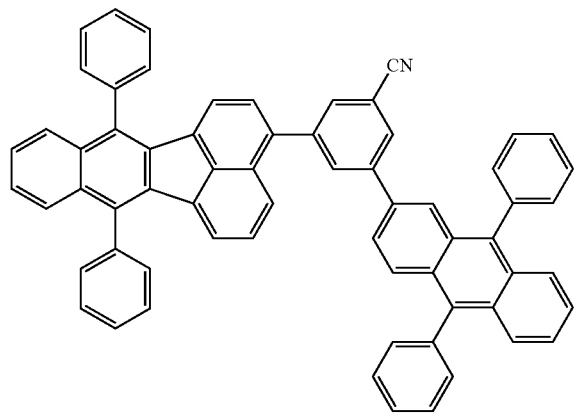
compound 11
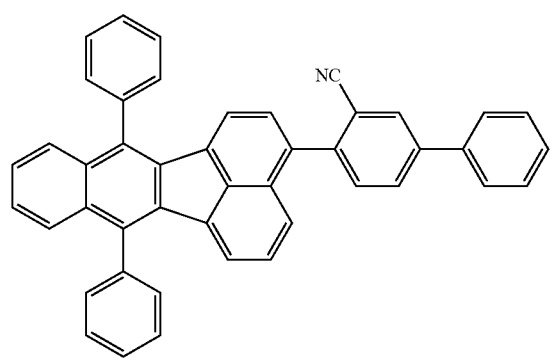
compound 12
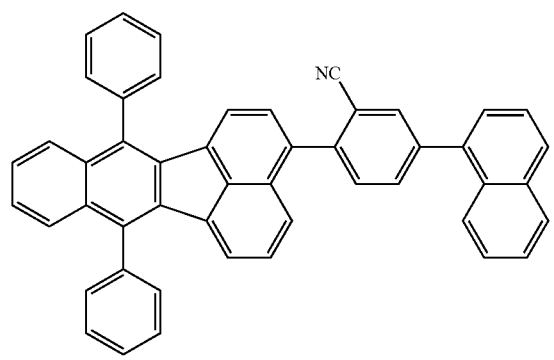
compound 13
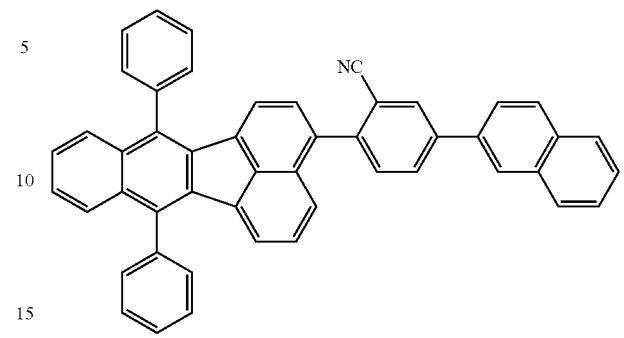
compound 14
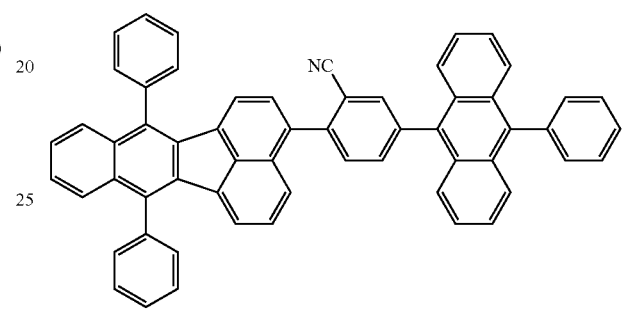
compound 15
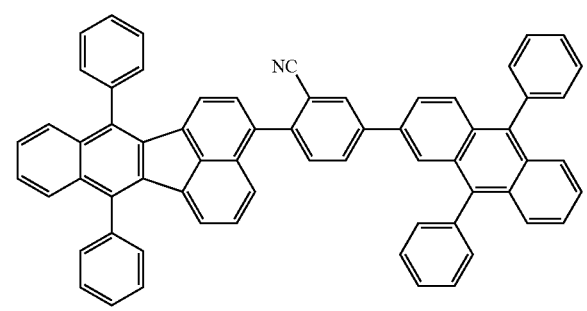
compound 16
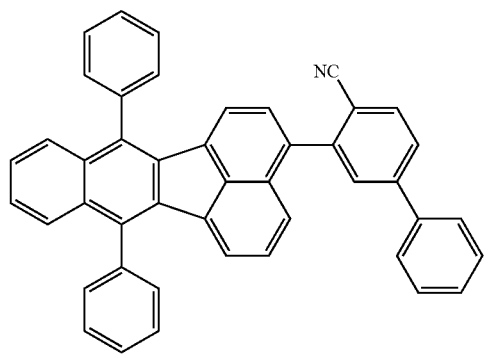

compound 17
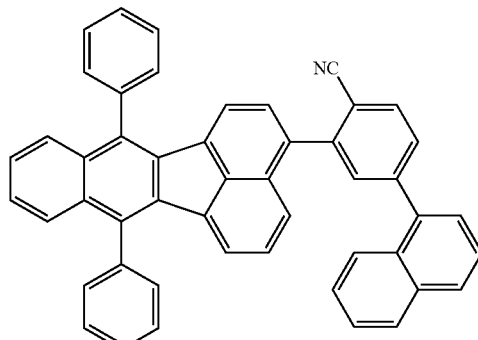
compound 18
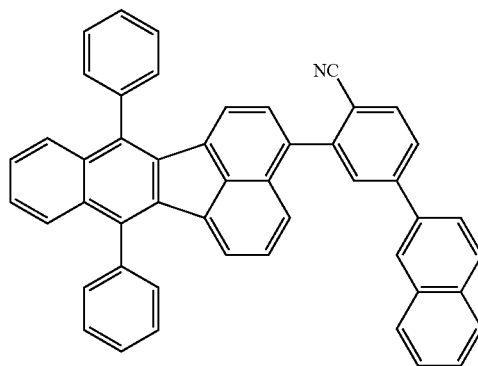
compound 19
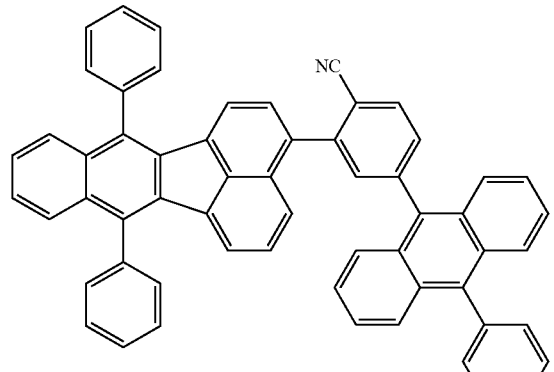
compound 20
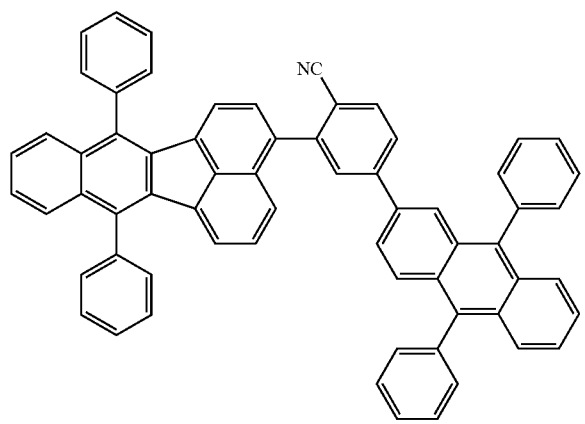
compound 21
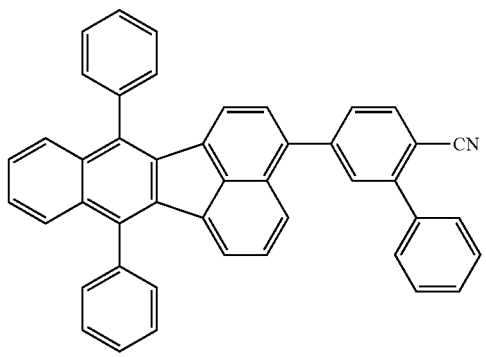
compound 22
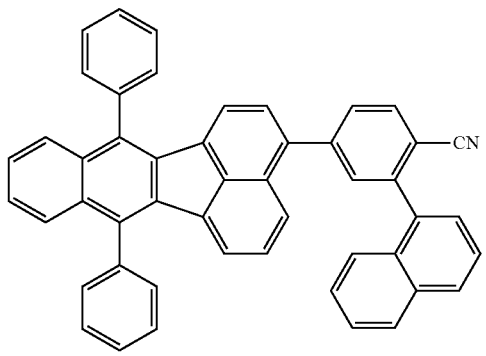
compound 23
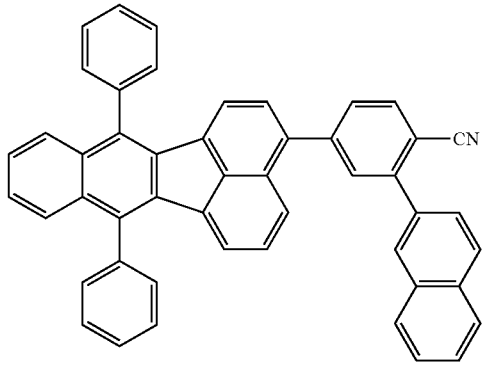
compound 24
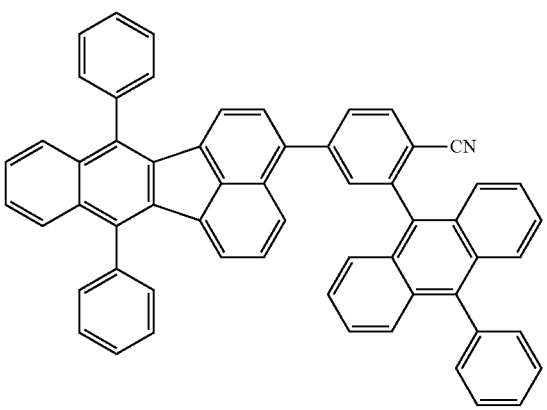

-continued compound 25

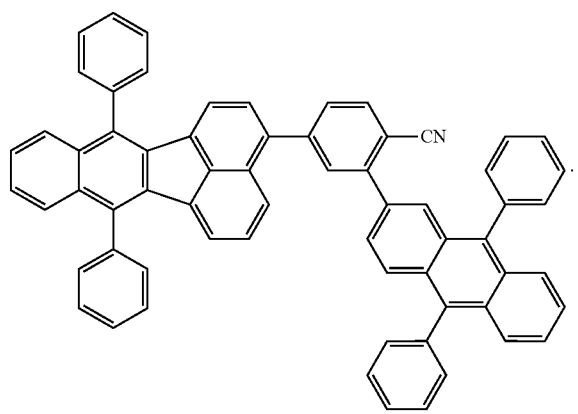

Synthesis of Organic Emitting Compounds

1. Synthesis of Compound 1

(1) Compound 1A [2-(7,12-diphenylbenzo[k]fluoranthen-3-yl)-4,4,5,5-tetramethyl-1,3,2-dioxaborolane]

[Reaction Formula 1-1]

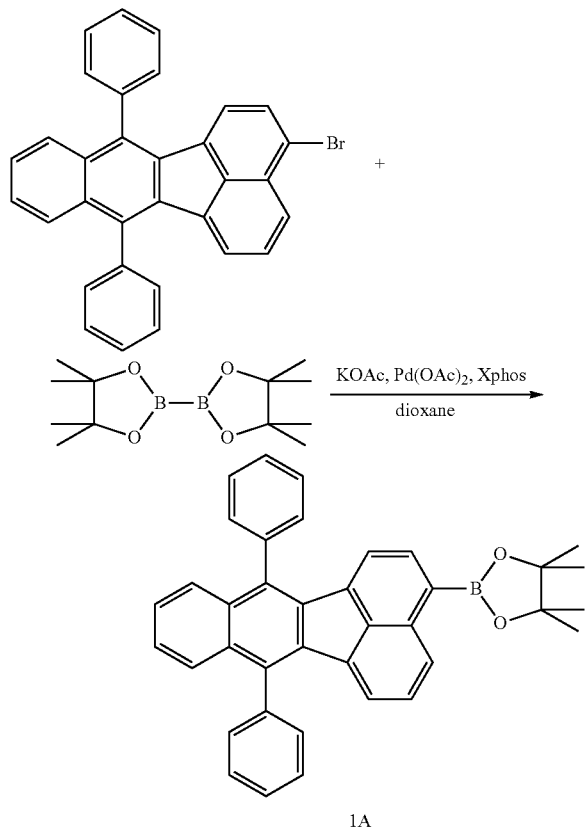

After 3-bromo-7,12-diphenylbenzo[k]fluoranthene (20.0 g, 41.4 mmol), bis(pinacolato)diboron (21.0 g, 82.8 mmol), potassium acetate(KOAc) (12.2 g, 124.1 mmol), palladium (II) acetate(Pd(OAc)$_2$) (0.37 g, 1.7 mmol), Xphos (3.2 g, 6.6 mmol) and dioxane (600 ml) were put into the rounded-bottom flask (1000 ml), and nitrogen gas is purged. The mixture was stirred under the temperature of 110° C. for 10 hrs. After completion of reaction, the organic layer is extracted using dichloromethane and distilled water, and the solvent was removed by the reduced-pressure distillation. The column chromatography using hexane and dichloromethane was performed to the crude product such that compound 1A was obtained. (15.3 g, yield: 70%)

(2) Compound 1B [4-bromo-[1,1'-biphenyl]-2-carbonitrile]

[Reaction Formula 1-2]

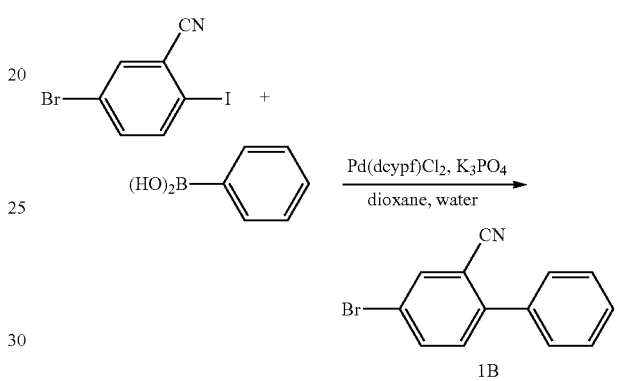

After 5-bromo-2-iodobenzonitrile (8.0 g, 26.0 mmol), phenylboronic acid (3.5 g, 28.6 mmol), potassium phosphate (13.8 g, 65.0 mmol), 1,1'-bis(di-cyclohexylphosphino)ferrocene]dichloropalladium(II) (0.4 g, 0.5 mmol), dioxane (50 ml) and water (15 ml) were put into the rounded-bottom flask (500 ml), and nitrogen gas is purged. The mixture was stirred under the temperature of 90° C. for 5 hrs. After completion of reaction, the organic layer is extracted using dichloromethane and distilled water, and the solvent was removed by the reduced-pressure distillation. The column chromatography using hexane and dichloromethane was performed to the crude product such that compound 1B was obtained. (3.5 g, yield: 52%)

(3) Compound 1 [4-(7,12-diphenylbenzo[k]fluoranthen-3-yl)-[1,1'-biphenyl]-2-carbonitrile]

[Reaction Formula 1-3]

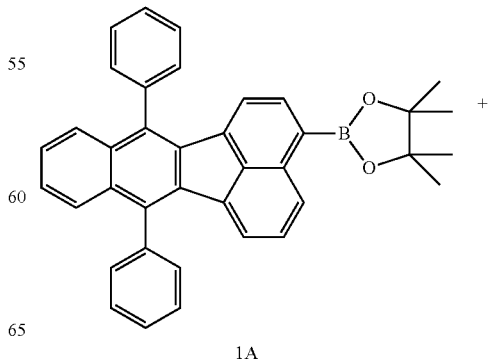

1A

-continued

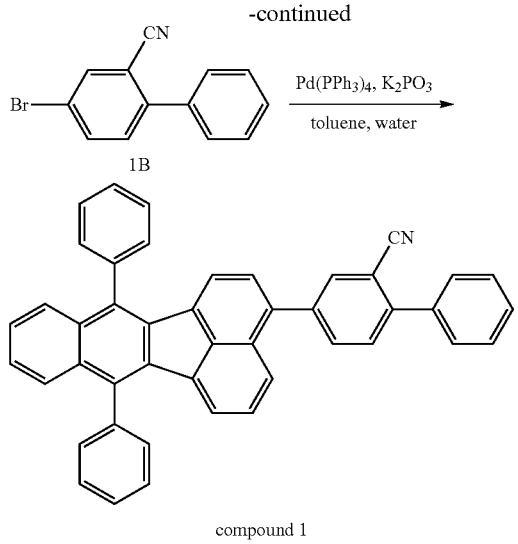

compound 1

After compound 1A (3.0 g, 5.7 mmol), compound 1B (1.6 g, 6.2 mmol), potassium carbonate (3.1 g, 22.6 mmol), tetrakis(triphenylphosphine)palladium(0.3 g, 0.3 mmol), toluene (30 ml), water (10 ml) and tetrahydrofuran(THF) (5 ml) were put into the rounded-bottom flask (500 ml), and nitrogen gas is purged. The mixture was stirred under the temperature of 90° C. for 10 hrs. After completion of reaction, the organic layer is extracted using dichloromethane and distilled water, and the solvent was removed by the reduced-pressure distillation. The column chromatography using hexane and dichloromethane was performed to the crude product such that compound 1 was obtained. (2.5 g, yield: 76%)

2. Synthesis of Compound 3

(1) Compound 3A [5-bromo-2-(naphthalen-2-yl)benzonitrile]

[Reaction Formula 2-1]

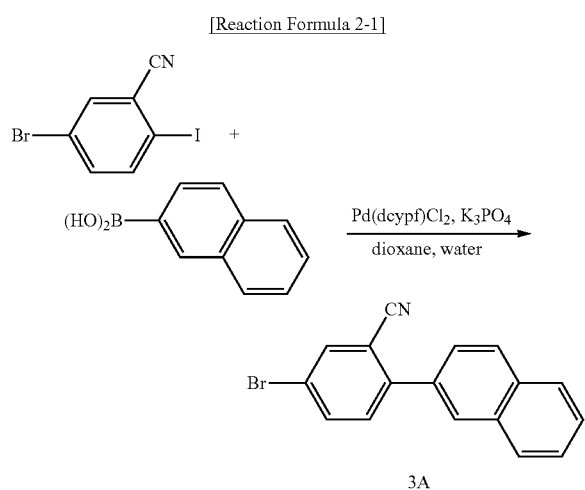

After 5-bromo-2-iodobenzonitrile (5.0 g, 16.2 mmol), naphthalen-2-ylboronic acid (3.1 g, 17.9 mmol), potassium phosphate (8.6 g, 40.6 mmol), 1,1'-bis(di-cyclohexylphosphino)ferrocene]dichloropalladium(II) (0.3 g, 0.3 mmol), dioxane (50 ml) and water (15 ml) were put into the rounded-bottom flask (500 ml), and nitrogen gas is purged. The mixture was stirred under the temperature of 90° C. for 5 hrs. After completion of reaction, the organic layer is extracted using dichloromethane and distilled water, and the solvent was removed by the reduced-pressure distillation. The column chromatography using hexane and dichloromethane was performed to the crude product such that compound 3A was obtained. (3.3 g, yield: 66%)

(2) Compound 3 [5-(7,12-diphenylbenzo[k]fluoranthen-3-yl)-2-(naphthalen-2-yl)benzonitrile]

[Reaction Formula 2-2]

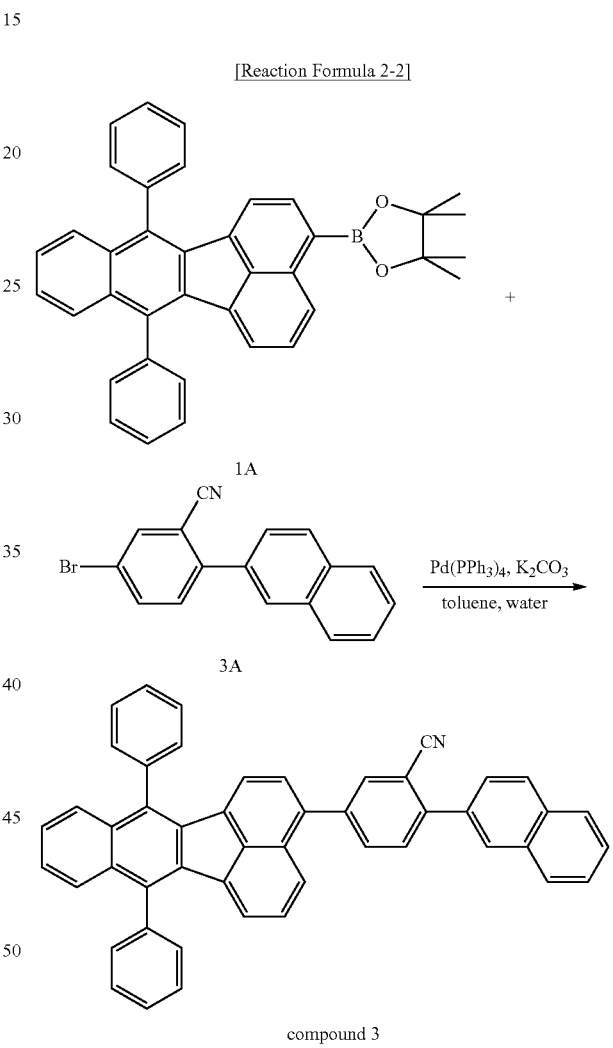

compound 3

After compound 1A (3.0 g, 5.7 mmol), compound 3A (1.9 g, 6.2 mmol), potassium carbonate (3.1 g, 22.6 mmol), tetrakis(triphenylphosphine)palladium(0.3 g, 0.3 mmol), toluene (30 ml), water (10 ml) and THF (5 ml) were put into the rounded-bottom flask (500 ml), and nitrogen gas is purged. The mixture was stirred under the temperature of 90° C. for 10 hrs. After completion of reaction, the organic layer is extracted using dichloromethane and distilled water, and the solvent was removed by the reduced-pressure distillation. The column chromatography using hexane and dichloromethane was performed to the crude product such that compound 3 was obtained. (2.7 g, yield: 75%)

3. Synthesis of Compound 5

(1) Compound 5A [5-bromo-2-(9,10-diphenylanthracen-2-yl)benzonitrile]

(2) compound 5 [2-(9,10-diphenylanthracen-2-yl)-5-(7,12-diphenylbenzo[k]fluoranthen-3-yl)benzonitrile]

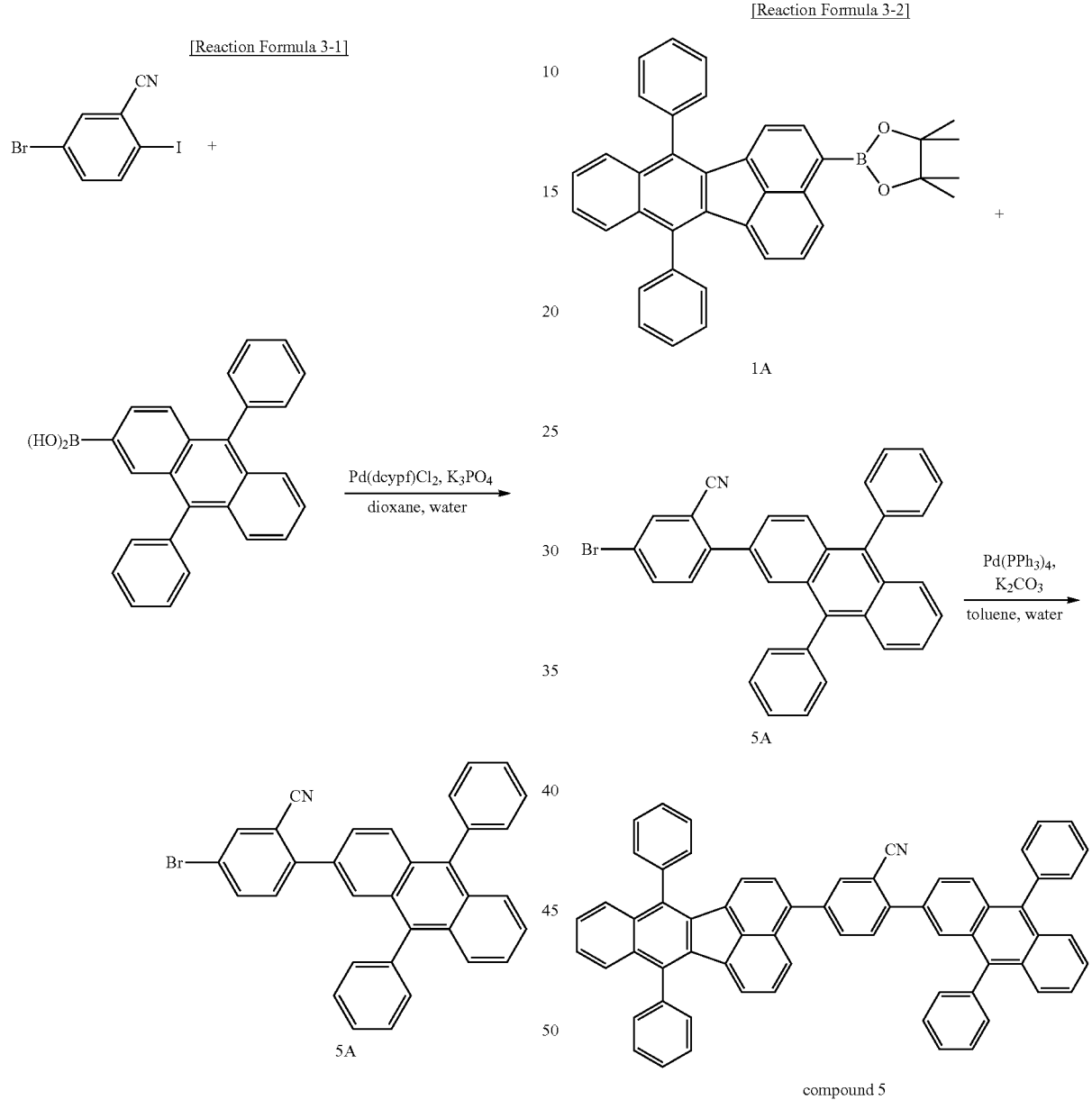

After 5-bromo-2-iodobenzonitrile (5.0 g, 16.2 mmol), (9,10-diphenylanthracen-2-yl)boronic acid (6.7 g, 17.9 mmol), potassium phosphate (8.6 g, 40.6 mmol), 1,1'-bis(di-cyclohexylphosphino)ferrocene]dichloropalladium(II) (0.3 g, 0.3 mmol), dioxane (50 ml) and water (15 ml) were put into the rounded-bottom flask (500 ml), and nitrogen gas is purged. The mixture was stirred under the temperature of 90° C. for 5 hrs. After completion of reaction, the organic layer is extracted using dichloromethane and distilled water, and the solvent was removed by the reduced-pressure distillation. The column chromatography using hexane and dichloromethane was performed to the crude product such that compound 5A was obtained. (5.2 g, yield: 63%)

After compound 1A (3.0 g, 5.7 mmol), compound 5A (3.2 g, 6.2 mmol), potassium carbonate (3.1 g, 22.6 mmol), tetrakis(triphenylphosphine)palladium(0.3 g, 0.3 mmol), toluene (30 ml), water (10 ml) and THF (5 ml) were put into the rounded-bottom flask (500 ml), and nitrogen gas is purged. The mixture was stirred under the temperature of 90° C. for 10 hrs. After completion of reaction, the organic layer is extracted using dichloromethane and distilled water, and the solvent was removed by the reduced-pressure distillation. The column chromatography using hexane and dichloromethane was performed to the crude product such that compound 5 was obtained. (3.0 g, yield: 64%)

4. Synthesis of Compound 10

(1) Compound 10A [3-bromo-5-(7,12-diphenyl-benzo[k]fluoranthen-3-yl)benzonitrile]

[Reaction Formula 4-1]

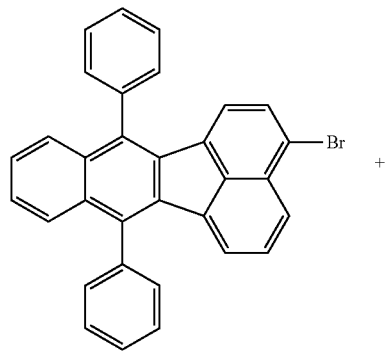

(2) Compound 10 [3-(9,10-diphenylanthracen-2-yl)-5-(7,12-diphenylbenzo[k]fluoranthen-3-yl)benzonitrile]

[Reaction Formula 4-2]

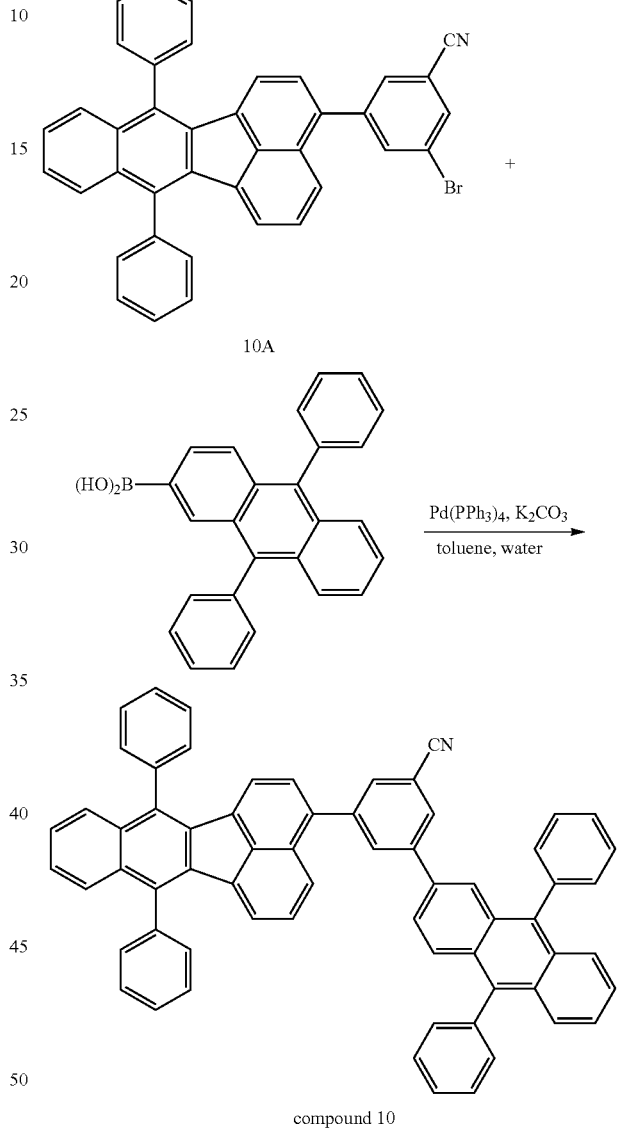

After 3-bromo-7,12-diphenylbenzo[k]fluoranthene (8.0 g, 16.6 mmol), 3-bromo-5-(4,4,5,5-tetramethyl-1,3,2-dioxaborolan-2-yl)benzonitrile (5.6 g, 18.2 mmol), potassium carbonate (9.1 g, 66.2 mmol), tetrakis(triphenylphosphine)palladium(1.0 g, 0.8 mmol), toluene (90 ml), water (30 ml) and THF (15 ml) were put into the rounded-bottom flask (500 ml), and nitrogen gas is purged. The mixture was stirred under the temperature of 90° C. for 10 hrs. After completion of reaction, the organic layer is extracted using dichloromethane and distilled water, and the solvent was removed by the reduced-pressure distillation. The column chromatography using hexane and dichloromethane was performed to the crude product such that compound 10A was obtained. (5.1 g, yield: 53%)

After compound 10A (4.5 g, 7.7 mmol), (9,10-diphenylanthracen-2-yl)boronic acid (3.2 g, 8.5 mmol), potassium carbonate (4.3 g, 30.1 mmol), tetrakis(triphenylphosphine)palladium(0.4 g, 0.4 mmol), toluene (45 ml), water (15 ml) and THF (5 ml) were put into the rounded-bottom flask (500 ml), and nitrogen gas is purged. The mixture was stirred under the temperature of 90° C. for 10 hrs. After completion of reaction, the organic layer is extracted using dichloromethane and distilled water, and the solvent was removed by the reduced-pressure distillation. The column chromatography using hexane and dichloromethane was performed to the crude product such that compound 10 was obtained. (3.6 g, yield: 56%)

5. Synthesis of Compound 15

(1) Compound 15A [5-bromo-2-(7,12-diphenyl-benzo[k]fluoranthen-3-yl)benzonitrile]

(2) Compound 15 [5-(9,10-diphenylanthracen-2-yl)-2-(7,12-diphenylbenzo[k]fluoranthen-3-yl)benzonitrile]

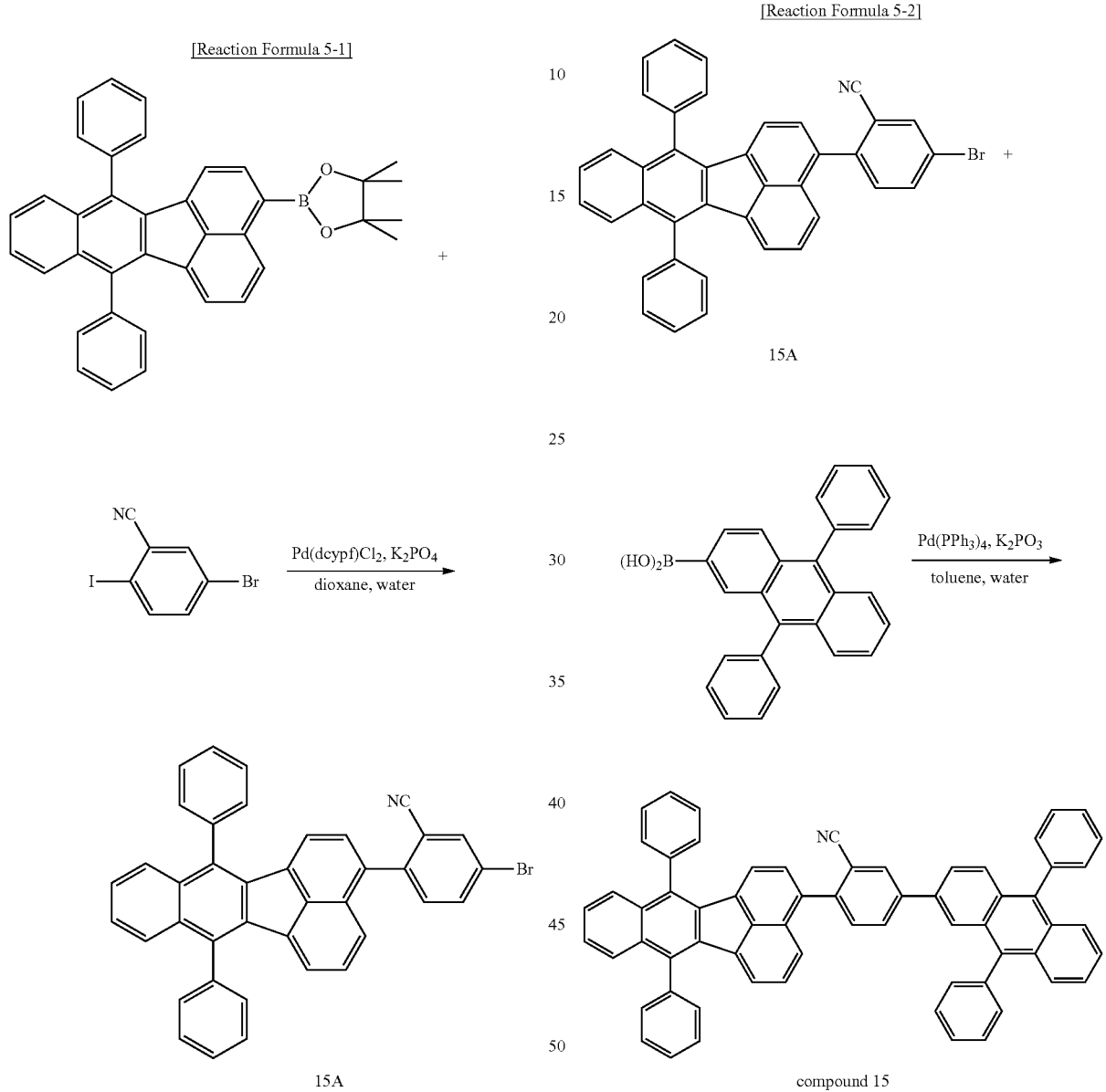

After compound 1A (8.0 g, 15.1 mmol), 5-bromo-2-iodobenzonitrile (5.1 g, 16.6 mmol), potassium phosphate (8.0 g, 37.7 mmol), 1,1'-bis(di-cyclohexylphosphino)ferrocene]dichloropalladium(II) (0.3 g, 0.3 mmol), dioxane (90 ml) and water (15 ml) were put into the rounded-bottom flask (500 ml), and nitrogen gas is purged. The mixture was stirred under the temperature of 90° C. for 5 hrs. After completion of reaction, the organic layer is extracted using dichloromethane and distilled water, and the solvent was removed by the reduced-pressure distillation. The column chromatography using hexane and dichloromethane was performed to the crude product such that compound 15A was obtained. (6.3 g, yield: 71%)

After compound 15A (3.5 g, 6.0 mmol), (9,10-diphenylanthracen-2-yl)boronic acid (2.5 g, 6.6 mmol), potassium carbonate (3.3 g, 23.9 mmol), tetrakis(triphenylphosphine)palladium(0.3 g, 0.3 mmol), toluene (45 ml), water (15 ml) and THF (5 ml) were put into the rounded-bottom flask (500 ml), and nitrogen gas is purged. The mixture was stirred under the temperature of 90° C. for 10 hrs. After completion of reaction, the organic layer is extracted using dichloromethane and distilled water, and the solvent was removed by the reduced-pressure distillation. The column chromatography using hexane and dichloromethane was performed to the crude product such that compound 15 was obtained. (3.1 g, yield: 62%)

6. Synthesis of Compound 21

(1) Compound 21A [5-bromo-[1,1'-biphenyl]-2-carbonitrile]

[Reaction Formula 6-1]

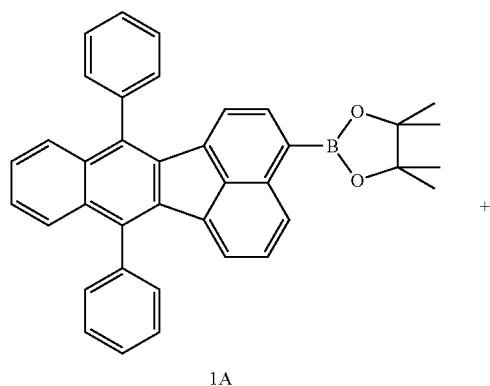

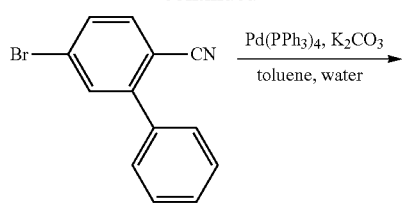

21A

After 4-bromo-2-iodobenzonitrile (6.0 g, 19.5 mmol), phenylboronic acid (2.6 g, 21.4 mmol), potassium phosphate (10.3 g, 48.7 mmol), 1,1'-bis(di-cyclohexylphosphino)ferrocene]dichloropalladium(II) (0.3 g, 0.4 mmol), dioxane (50 ml) and water (15 ml) were put into the rounded-bottom flask (500 ml), and nitrogen gas is purged. The mixture was stirred under the temperature of 90° C. for 6 hrs. After completion of reaction, the organic layer is extracted using dichloromethane and distilled water, and the solvent was removed by the reduced-pressure distillation. The column chromatography using hexane and dichloromethane was performed to the crude product such that compound 21A was obtained. (3.3 g, yield: 65%)

(2) Compound 21 [5-(7,12-diphenylbenzo[k]fluoranthen-3-yl)-[1,1'-biphenyl]-2-carbonitrile]

[Reaction Formula 6-2]

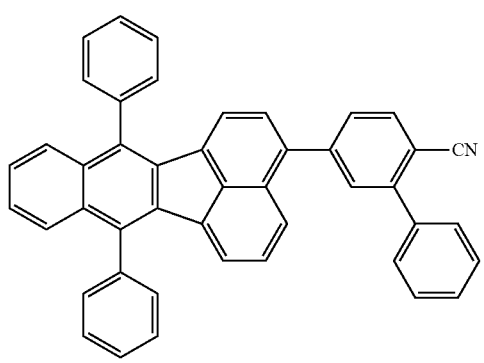

compound 21

After compound 1A (3.0 g, 5.7 mmol), compound 21 A (1.6 g, 6.2 mmol), potassium carbonate (3.1 g, 22.6 mmol), tetrakis(triphenylphosphine)palladium(0.3 g, 0.3 mmol), toluene (30 ml), water (10 ml) and THF (5 ml) were put into the rounded-bottom flask (500 ml), and nitrogen gas is purged. The mixture was stirred under the temperature of 90° C. for 10 hrs. After completion of reaction, the organic layer is extracted using dichloromethane and distilled water, and the solvent was removed by the reduced-pressure distillation. The column chromatography using hexane and dichloromethane was performed to the crude product such that compound 21 was obtained. (2.3 g, yield: 70%)

The maximum emission wavelength (λmax) and the FWHM of compounds 1, 3, 5, 10 and 15 in Formula 2 and compounds in Formulas 3 to 6 are measured and listed in Table 1.

[Formula 3]

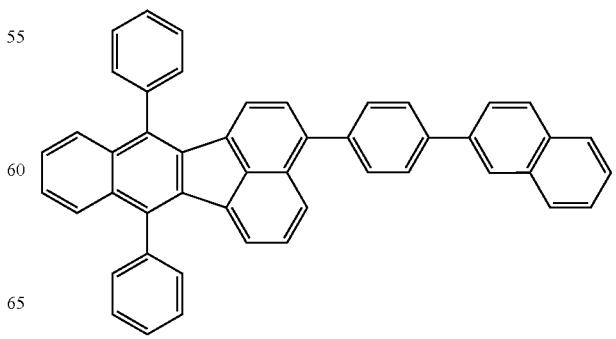

[Formula 4]

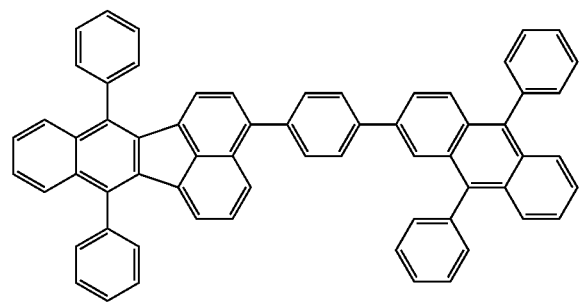

[Formula 5]

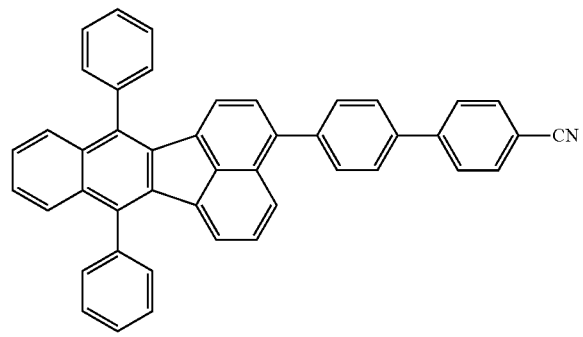

[Formula 6]

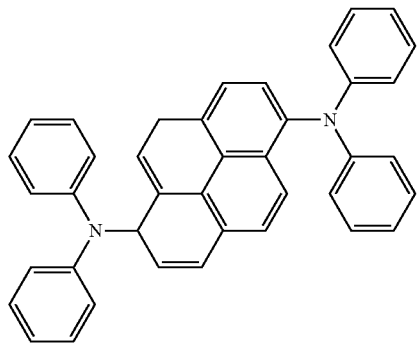

The compounds in Formulas 3 to 5 also includes a benzofluoranthene core without a cyanophenylene moiety directly bonded to the benzofluoranthene core. The compound in Formula 6 is the related art blue fluorescent dopant.

TABLE 1

|  | λmax [nm] | FWHM [nm] |
| --- | --- | --- |
| compound 1 | 443 | 50 |
| compound 3 | 443 | 48 |
| compound 5 | 450 | 46 |
| compound 10 | 448 | 48 |
| compound 15 | 449 | 45 |
| Formula 3 | 445 | 50 |
| Formula 4 | 451 | 52 |
| Formula 5 | 444 | 48 |
| Formula 6 | 461 | 51 |

As shown in Table 1, the organic emitting compound of the present disclosure has blue emission property and narrow FWHM. Namely, the organic emitting compound of the present disclosure includes the benzofluoranthene core and the cyanophenylene moiety, which is directly bonded to the benzofluoranthene core, such that blue emission with high color purity is provided.

The EML may further include a host. Namely, the organic emitting compound of the present disclosure is used as the dopant in the EML and is doped by approximately 1 to 30 wt % with respect to the host.

For example, one of the materials in Formula 7 may be used as the host. (Bis[2-(diphenylphosphino)phenyl]ether oxide (DPEPO), 2,8-bis(diphenylphosphoryl)dibenzothiophene (PPT), 2,8-di(9H-carbazol-9-yl)dibenzothiophene (DCzDBT), m-bis(carbazol-9-yl)biphenyl (m-CBP), Diphenyl-4-triphenylsilylphenyl-phosphine oxide (TPSO1), 9-(9-phenyl-9H-carbazol-6-yl)-9H-carbazole (CCP) in order.)

[Formula 7]

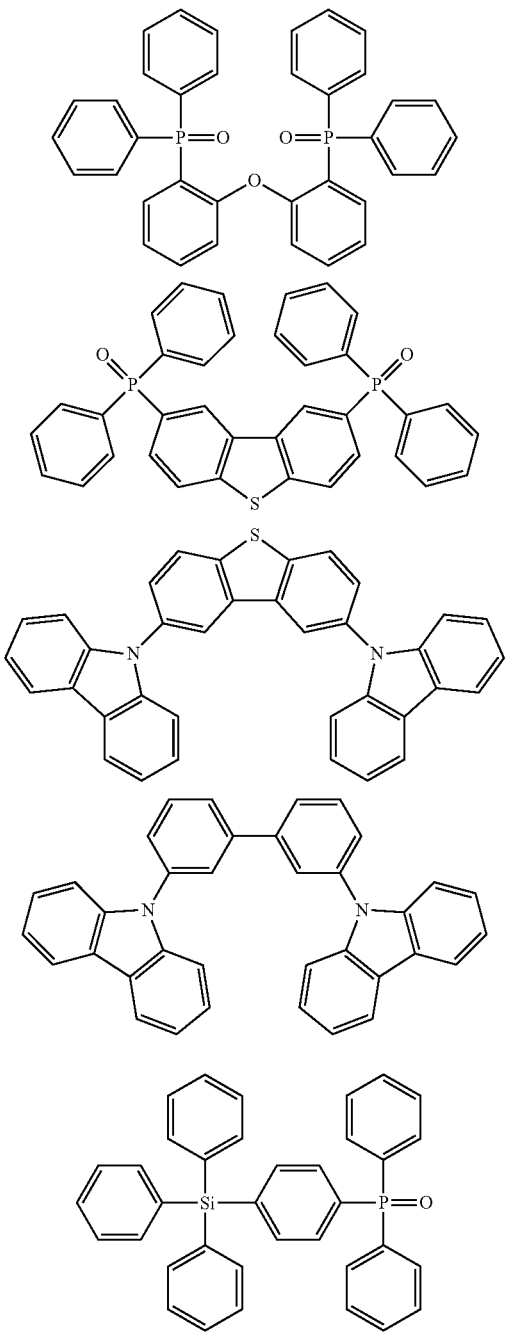

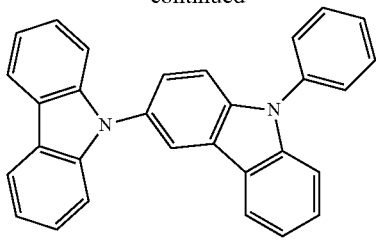

The EML 240 may further include a delayed fluorescent compound. Namely, in the EML 240, the organic emitting compound of the present disclosure is used as a first dopant (fluorescent dopant), and the delayed fluorescent compound is used as a second dopant (delayed fluorescent dopant). A summation of the organic emitting compound of the present disclosure and the delayed fluorescent compound may have a range of approximately 1 to 50 wt % with respect to the host.

The percentage by weight of the delayed fluorescent dopant may be greater than that of the fluorescent dopant. As a result, the energy transfer from the delayed fluorescent dopant into the fluorescent dopant is sufficiently generated.

In the delayed fluorescent compound, a difference between the energy level of singlet state of the dopant and the energy level of triplet state of the dopant is equal to or less than 0.3 eV. As a result, the energy level of triplet state of the delayed fluorescent dopant is converted into the energy level of singlet state of the delayed fluorescent dopant by the reverse intersystem crossing (RISC) effect.

Namely, the delayed fluorescent compound is configured such that a triplet exciton is activated by an electric field and is thus up-converted into a singlet exciton, and accordingly, both of the triplet exciton and the singlet exciton are involved in light emission.

Since the EML 240 includes both the organic emitting compound of the present disclosure as the fluorescent dopant and the delayed fluorescent dopant, the singlet energy and the triplet energy of the delayed fluorescent dopant are transferred into the organic emitting compound of the present disclosure as the fluorescent dopant and the emission is provided from the organic emitting compound of the present disclosure as the fluorescent dopant. As result, the quantum efficiency of the OLED D is increased, and the FWHM of the OLED D is narrowed.

Figure 3:
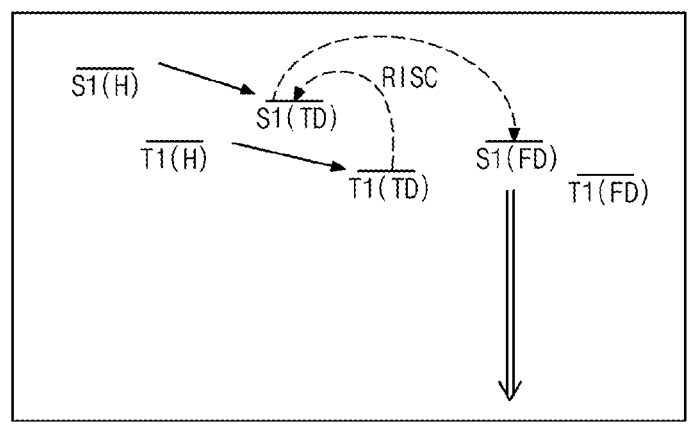
FIG. 3 is a view explaining a light emission mechanism in an OLED according to an embodiment of the present disclosure.

Referring to FIG. 3, which is a view explaining a light emission mechanism in an OLED, the exciton at the energy level of the triplet state ($E_{T1}$(TD)) of the delayed fluorescent dopant is converted into the exciton at the energy level of the singlet state ($E_{s1}$(TD)) by the effect of the reverse intersystem crossing (RISC), and the exciton at the energy level of the singlet state ($E_{s1}$(TD)) of the delayed fluorescent dopant is transferred into the energy level of the singlet state ($E_{s1}$(FD)) of the fluorescent dopant by an effect of Foster resonance energy transfer. As a result, the light is emitted from the fluorescent dopant.

The energy level of the singlet state ($E_{S1}$(H)) of the host is greater than the energy level of the singlet state ($E_{S1}$(TD)) of the delayed fluorescent dopant. In addition, the energy level of the triplet state ($E_{T1}$(TD)) of the delayed fluorescent dopant is smaller than the energy level of the triplet state ($E_{T1}$(H)) of the host and greater than the energy level of the triplet state ($E_{T1}$(FD)) of fluorescent dopant. Moreover, the energy level of the singlet state ($E_{S1}$(H)) of the host is greater than the energy level of the singlet state ($E_{S1}$(FD)) of the fluorescent dopant.

When not satisfying this condition, a quenching happens at the delayed fluorescent dopant and/or the fluorescent dopant or an energy transfer from the host to the delayed fluorescent dopant does not happen, and thus the quantum efficiency of the OLED D is reduced.

A difference between the energy level of the HOMO of the delayed fluorescent dopant and the energy level of the HOMO of the organic emitting compound as the fluorescent dopant is equal to or less than 0.3 eV. If the difference is greater than 0.3 eV, the hole is trapped in the HOMO level of the fluorescent dopant such that high quantum efficiency of the delayed fluorescent dopant cannot be provided.

Figure 4A:
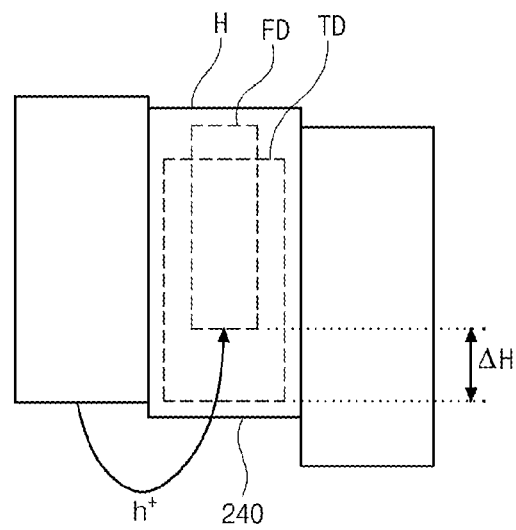
FIGS. 4A and 4B are views explaining an energy band diagram in an organic emitting layer of an OLED according to an embodiment of the present disclosure.

As shown in FIG. 4A, when the difference (ΔH) between the energy level of the HOMO of the fluorescent dopant (FD) and the energy level of the HOMO of the delayed fluorescent dopant (TD) is too big (e.g., ΔH>0.3 eV), the hole (h+) from the anode is transferred into the fluorescent dopant (FD) such that the emission directly happens from the fluorescent dopant. In this instance, the narrow FWHM by the fluorescent dopant is provided, but high quantum efficiency by the delayed fluorescent dopant cannot be provided.

Figure 4B:
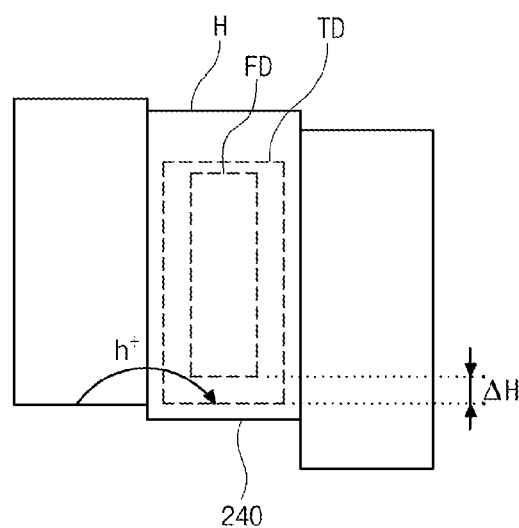

However, as shown in FIG. 4B, when the difference (ΔH) between the energy level of the HOMO of the fluorescent dopant (FD) and the energy level of the HOMO of the delayed fluorescent dopant (TD) is equal to or less than approximately 0.3 eV (ΔH≤0.3 eV), the hole (h+) is transferred into the delayed fluorescent dopant (TD) such that the exciton is generated in the delayed fluorescent dopant. Accordingly, the emission happens from the fluorescent dopant (FD) by the above energy transfer, and high quantum efficiency by the delayed fluorescent dopant (TD) and narrow FWHM by the fluorescent dopant (FD) are provided.

The energy level of the HOMO of the compound of Formula 8, which may be used as the delayed fluorescent dopant (TD), the compounds 1, 3, 5, 10 and 15 of Formula 2, and the compounds of Formulas 3 to 6 are measured and listed in Table 2.

[Formula 8]

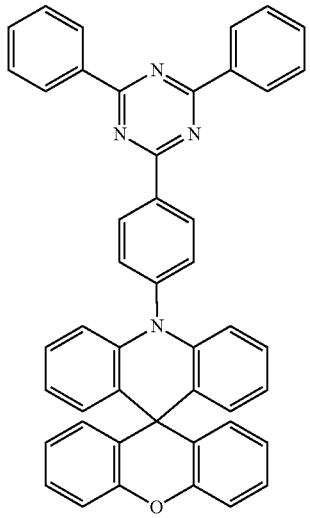

The energy level of the HOMO is measured by the cyclic voltammetry.

TABLE 2

|  | HOMO (eV) |
| --- | --- |
| TD | 5.50 |
| compound 1 | 5.32 |
| compound 3 | 5.30 |
| compound 5 | 5.29 |
| compound 10 | 5.26 |
| compound 15 | 5.25 |
| Formula 3 | 5.08 |
| Formula 4 | 5.07 |
| Formula 5 | 5.11 |
| Formula 6 | 5.04 |

As shown in Table 2, the organic emitting compound of the present disclosure has deep HOMO level. Namely, since the organic emitting compound of the present disclosure includes the benzofluoranthene core and the cyanophenylene moiety, which is directly bonded to the benzofluoranthene core, the organic emitting compound has deep HOMO level. Accordingly, the difference between the energy level of the HOMO of the delayed fluorescent dopant and the energy level of the HOMO of the organic emitting compound as the fluorescent dopant is equal to or less than 0.3 eV.

When the EML of the OLED includes the organic emitting compound as a first dopant and the delayed fluorescent compound as a second dopant, the quantum efficiency and the color purity are improved.

[OLED]

Following layers are sequentially deposited on an ITO layer (anode).

(a) HIL (50 Å, compound of Formula 9-1 (HATCN)), (b) HTL (500 Å, compound of Formula 9-2 (NPB)), (c) EBL (100 Å, compound of Formula 9-3), (d) EML (300 Å, Host (DPEPO: TD (compound of Formula 8, 27 wt %): FD (3 wt %)), (e) HBL (100 Å, DPEP)), (f) ETL (250 Å, compound of Formula 9-4 (TPBi)), (g) EIL (8 Å, LiF), and (h) Cathode (1000 Å, Al)

[Formula 9-1]

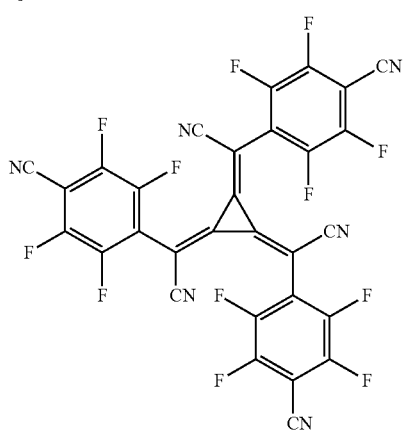

[Formula 9-2]

[Formula 9-3]

[Formula 9-4]

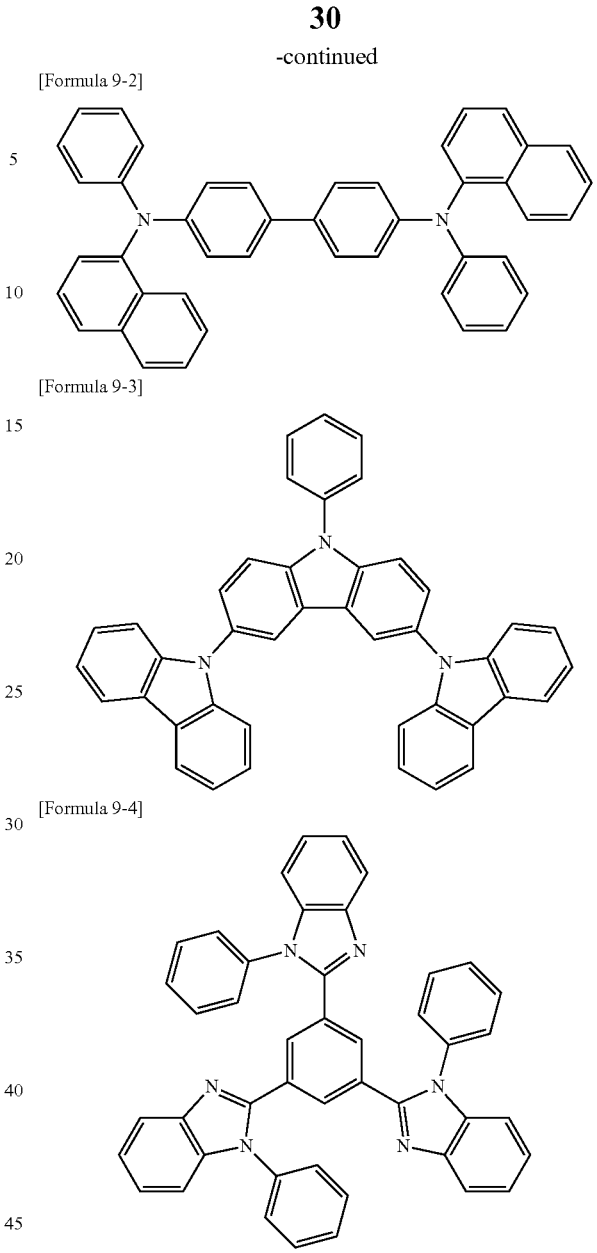

(1) Example 1 (Ex1)

The compound 1 is used as the fluorescent dopant (FD) in the EML.

(2) Example 2 (Ex2)

The compound 3 is used as the fluorescent dopant (FD) in the EML.

(3) Example 3 (Ex3)

The compound 5 is used as the fluorescent dopant (FD) in the EML.

(4) Example 4 (Ex4)

The compound 10 is used as the fluorescent dopant (FD) in the EML.

(5) Example 5 (Ex5)

The compound 15 is used as the fluorescent dopant (FD) in the EML.

(6) Comparative Example 1 (Ref1)

The compound of Formula 3 is used as the fluorescent dopant (FD) in the EML.

(7) Comparative Example 2 (Ref2)

The compound of Formula 4 is used as the fluorescent dopant (FD) in the EML.

(8) Comparative Example 3 (Ref3)

The compound of Formula 5 is used as the fluorescent dopant (FD) in the EML.

(9) Comparative Example 4 (Ref4)

The compound of Formula 6 is used as the fluorescent dopant (FD) in the EML.

The properties, i.e., the driving voltage ([V]), the current efficiency ([cd/A]), the power efficiency ([lm/W]), the CIE color coordinate, the maximum EL (ELmax) and the external quantum efficiency (EQE), of the organic light emitting diodes of Examples 1 to 5 and Comparative Examples 1 to 4 are measured and listed in Table 3.

TABLE 3

|  | V | cd/A | lm/W | CIEx | CIEy | ELmax (nm) | EQE (%) |
|---|---|---|---|---|---|---|---|
| Ex1 | 4.2 | 15.0 | 11.2 | 0.140 | 0.153 | 448 | 12.2 |
| Ex2 | 4.3 | 15.7 | 11.5 | 0.146 | 0.154 | 448 | 12.3 |
| Ex3 | 4.3 | 18.3 | 13.3 | 0.151 | 0.161 | 451 | 13.0 |
| Ex4 | 4.5 | 14.3 | 10.0 | 0.148 | 0.161 | 450 | 11.1 |
| Ex5 | 4.3 | 12.5 | 9.2 | 0.150 | 0.163 | 452 | 10.2 |
| Ref1 | 5.6 | 10.5 | 5.9 | 0.140 | 0.150 | 447 | 5.6 |
| Ref2 | 5.5 | 10.3 | 5.8 | 0.149 | 0.164 | 453 | 6.8 |
| Ref3 | 5.1 | 11.0 | 6.8 | 0.142 | 0.148 | 445 | 7.0 |
| Ref4 | 5.8 | 11.7 | 6.3 | 0.147 | 0.171 | 462 | 6.1 |

As shown in Table 3, in comparison to the OLED in Comparative Examples 1 to 4, the OLED of Examples 1 to 5 including the organic emitting compound of the present disclosure, which includes the benzofluoranthene core and the cyanophenylene moiety, which is directly bonded to the benzofluoranthene core, in the EML and the delayed fluorescent dopant has improved emitting efficiency and reduced power consumption.

Figure 5:
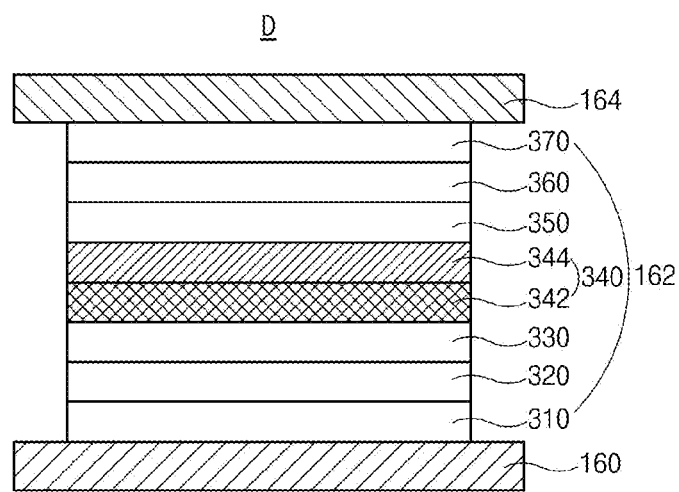
FIG. 5 is a schematic-cross sectional view of an OLED according to a second embodiment of the present disclosure.

FIG. 5 is a schematic-cross sectional view of an OLED according to a second embodiment of the present disclosure.

As shown in FIG. 5, an OLED D includes the first electrode 160 and the second electrode 164, which face each other, and the organic emitting layer 162 therebetween. The organic emitting layer 162 includes an EML 340, which includes first and second layers 342 and 344 and is positioned between the first and second electrodes 160 and 164, an HTL 320 between the first electrode 160 and the EML 340 and an ETL 360 between the second electrode 164 and the EML 340.

In addition, the organic emitting layer 162 may further include a HIL 310 between the first electrode 160 and the HTL 320 and an EIL 370 between the second electrode 164 and the ETL 360.

Moreover, the organic emitting layer 162 may further include an EBL 330 between the HTL 320 and the EML 340 and a HBL 350 between the EML 340 and the ETL 360.

For example, in the EML 340, one of the first layer 342 (e.g., a first emitting material layer) and the second layer 344 (e.g., a second emitting material layer) may include the organic emitting compound of the present disclosure as a first dopant (a fluorescent dopant) and a delayed fluorescent compound as a second dopant (a first delayed fluorescent dopant), and a host (a first host). The other one of the first and second layers 342 and 344 may include a delayed fluorescent compound as a third dopant (a second delayed fluorescent dopant) and a second host.

The first host may be selected from the materials of Formula 7, and the second host may be same as or different from the first host. The first and second delayed fluorescent dopants may be same.

The organic light emitting diode, where the first layer 342 includes the fluorescent dopant, the first delayed fluorescent dopant, and the first host, will be explained.

In the first layer 342, a summation of the fluorescent dopant and the first delayed fluorescent dopant may be approximately 1 to 50 wt % with respect to the first host. In the second layer 344, the second delayed fluorescent dopant may have approximately 1 to 30 wt % with respect to the second host.

In the OLED D, since the first layer 342 of the EML 340 includes the organic emitting compound of the present disclosure as the fluorescent dopant and the first delayed fluorescent dopant, the singlet energy and the triplet energy of the first delayed fluorescent dopant are transferred into the fluorescent dopant, i.e., the organic emitting compound of the present disclosure, such that the emission is generated from the fluorescent dopant. Accordingly, the quantum efficiency of the OLED D is increased, and the FWHM of the OLED D is narrowed.

On the other hand, when the amount, i.e., percentage by weight, of the first delayed fluorescent dopant is increased to increase the energy efficiency in the first layer 342, the quenching may happen in the first delayed fluorescent dopant such that the emitting efficiency may be decreased.

However, in the OLED of the present disclosure, since the OLED D includes the second layer 344, which is adjacent to the first layer 342 and includes the second delayed fluorescent dopant, without increasing the amount of the first delayed fluorescent dopant in the first layer 342, the energy efficiency is increased without the quenching problem.

Namely, the singlet energy of the first delayed fluorescent dopant in the first layer 342 and the singlet energy of the second delayed fluorescent dopant in the second layer 344 are transferred into the fluorescent dopant in the first layer 342 such that the emission happens from the fluorescent dopant.

The percentage by weight of the first delayed fluorescent dopant in the first layer 342 may be smaller than that of the fluorescent dopant in the first layer 342 and/or that of the second delayed fluorescent dopant in the second layer 344.

For example, the second host, which is included in the second layer 344 with the second delayed fluorescent dopant, may be same as a material of the HBL 350. In this instance, the second layer 344 may have a hole blocking function with an emission function. Namely, the second layer 344 may serve as a buffer layer for blocking the hole. When the HBL 350 is omitted, the second layer 344 serves as an emitting layer and a hole blocking layer.

When the first layer 342 includes the second delayed fluorescent dopant and the second layer 344 includes the fluorescent dopant, i.e., the organic emitting compound of the present disclosure, the first delayed fluorescent dopant, the host of the first layer 342 may be same as a material of the EBL 330. In this instance, the first layer 342 may have an electron blocking function with an emission function. Namely, the first layer 342 may serve as a buffer layer for blocking the electron. When the EBL 330 is omitted, the first layer 342 serves as an emitting layer and an electron blocking layer.

Alternatively, in the EML 340, one of the first layer 342 and the second layer 344 may include the organic emitting compound of the present disclosure as a first dopant (a first fluorescent dopant) and a delayed fluorescent compound as a second dopant (a delayed fluorescent dopant), and a host (a first host), and the other one of the first and second layers 342 and 344 may include a fluorescent compound as a third dopant (a second fluorescent dopant) and a second host.

The first host may be selected from the materials of Formula 7, and the second host may be same as or different from the first host. The first and second fluorescent dopants may be same.

When the amount, i.e., percentage by weight, of the first fluorescent dopant is increased to increase the brightness by the first fluorescent dopant in the first layer 342, the quenching may happen in the first fluorescent dopant such that the emitting efficiency may be decreased.

However, in the OLED of the present disclosure, since the OLED D includes the second layer 344, which is adjacent to the first layer 342 and includes the second fluorescent dopant, without increasing the amount of the first fluorescent dopant in the first layer 342, the brightness is increased without the quenching problem.

Namely, the singlet energy of the delayed fluorescent dopant in the first layer 342 is transferred into the first fluorescent dopant in the first layer 342 and the second fluorescent dopant in the second layer 344 such that the emission happens from the first and second fluorescent dopants. Accordingly, the brightness of the OLED D is improved without the quenching problem in the fluorescent dopant.

In this instance, the percentage by weight of the delayed fluorescent dopant in the first layer 342 may be greater than that of the first fluorescent dopant in the first layer 342 and smaller than that of the second fluorescent dopant in the second layer 344. In addition, the percentage by weight of the first fluorescent dopant in the first layer 342 may be smaller than that of the second fluorescent dopant in the second layer 344.

For example, the second host, which is included in the second layer 344 with the second fluorescent dopant, may be same as a material of the HBL 350. In this instance, the second layer 344 may have a hole blocking function with an emission function. Namely, the second layer 344 may serve as a buffer layer for blocking the hole. When the HBL 350 is omitted, the second layer 344 serves as an emitting layer and a hole blocking layer.

When the first layer 342 includes the second fluorescent dopant and the second layer 344 includes the first fluorescent dopant and the delayed fluorescent dopant, the host of the first layer 342 may be same as a material of the EBL 330. In this instance, the first layer 342 may have an electron blocking function with an emission function. Namely, the first layer 342 may serve as a buffer layer for blocking the electron. When the EBL 330 is omitted, the first layer 342 serves as an emitting layer and an electron blocking layer.

Figure 6:
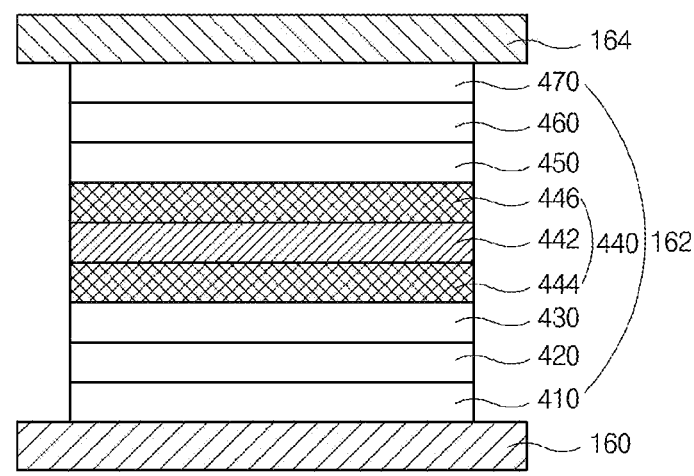
FIG. 6 is a schematic-cross sectional view of an OLED according to a third embodiment of the present disclosure.

FIG. 6 is a schematic-cross sectional view of an OLED according to a third embodiment of the present disclosure.

As shown in FIG. 6, an organic light emitting diode D includes the first and second electrodes 160 and 164, which face each other, and the organic emitting layer 162 therebetween. The organic emitting layer 162 includes an EML 440, which includes first to third layers 442, 444 and 446 and is positioned between the first and second electrodes 160 and 164, a HTL 420 between the first electrode 160 and the EML 440 and an ETL 460 between the second electrode 164 and the EML 440.

In addition, the organic emitting layer 162 may further include a HIL 410 between the first electrode 160 and the HTL 420 and an EIL 470 between the second electrode 164 and the ETL 460.

Moreover, the organic emitting layer 162 may further include an EBL 430 between the HTL 420 and the EML 440 and a HBL 450 between the EML 440 and the ETL 460.

In the EML 440, the first layer 442 is positioned between the second layer 444 and the third layer 446. Namely, the second layer 444 is positioned between the EBL 430 and the first layer 442, and the third layer 446 is positioned between the first layer 442 and the HBL 450.

The first layer 442 (e.g., a first emitting material layer) may include a fluorescent compound as a first dopant (a first fluorescent dopant), and each of the second and third layers 444 and 446 includes the organic emitting compound of the present disclosure as a second dopant (a second fluorescent dopant) and a delayed fluorescent compound as a third dopant (delayed fluorescent dopant). The delayed fluorescent dopant in the second layer 444 and the delayed fluorescent dopant in the third layer 446 may be same or different.

In the OLED D, since the second layer 444 and the third layer 446 of the EML 440 includes the organic emitting compound of the present disclosure as the fluorescent dopant and the delayed fluorescent dopant, the singlet energy and the triplet energy of the delayed fluorescent dopant are transferred into the fluorescent dopant, i.e., the organic emitting compound of the present disclosure, such that the emission is generated from the fluorescent dopant. Accordingly, the quantum efficiency of the OLED D is increased, and the FWHM of the OLED D is narrowed.

In each of the second and third layers 444 and 446, the percentage by weight of the delayed fluorescent dopant may be greater than that of the second fluorescent dopant. As a result, the energy transfer from the delayed fluorescent dopant into the second fluorescent dopant is sufficiently generated such that the quantum efficiency of the OLED D is improved.

On the other hand, since the amount of the second fluorescent dopant is relatively small in the second and third layers 444 and 446, the brightness of the OLED D may be insufficient.

However, in the OLED D of the present disclosure, since the first layer 442, which includes the first fluorescent dopant, is positioned between the second layer 444 and the third layer 446, each of which includes the delayed fluorescent dopant and the second fluorescent dopant, the energy is transferred from the delayed fluorescent dopant into the first and second fluorescent dopant, and thus the emission happens from the first and second dopants. Accordingly, the brightness of the OLED D is improved.

The percentage by weight of the delayed fluorescent dopant in each of the second and third layers 444 and 446 may be greater than that of the second fluorescent dopant in each of the second and third layers 444 and 446 and smaller than that of the first fluorescent dopant in the first layer 442 such that the energy transfer efficiency and the brightness are improved.

It will be apparent to those skilled in the art that various modifications and variations can be made in the present disclosure without departing from the spirit or scope of the present disclosure. Thus, it is intended that the present disclosure cover the modifications and variations of the present disclosure provided they come within the scope of the appended claims and their equivalents.

What is claimed is:

1. An organic emitting compound being selected from the group consisting of:

compound 2 compound 3 compound 4 compound 5
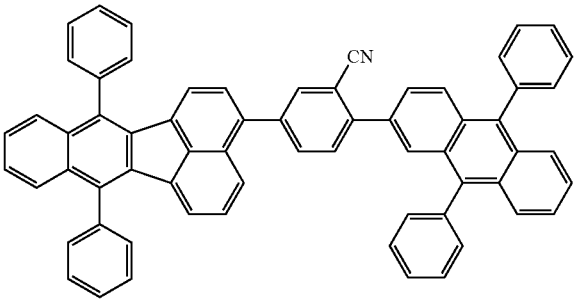

compound 7
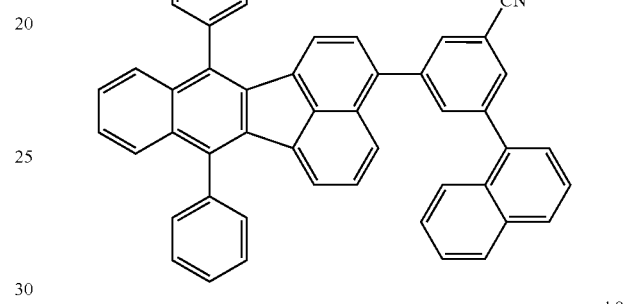

compound 8
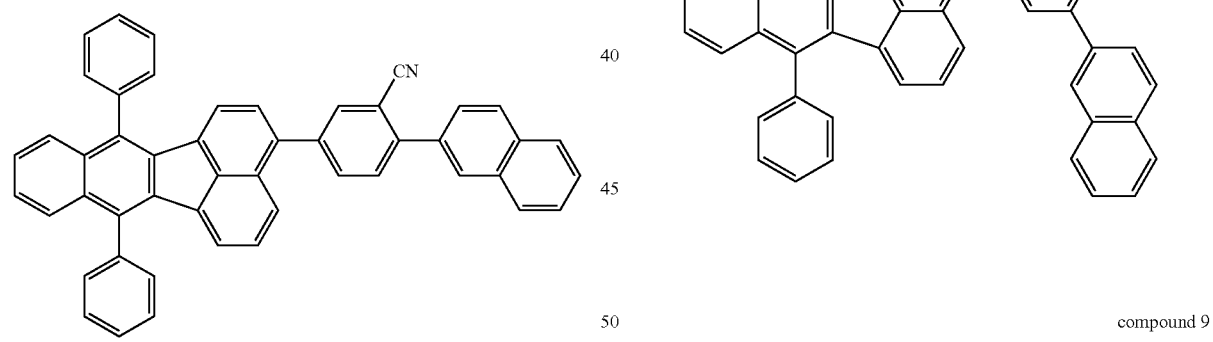

compound 9
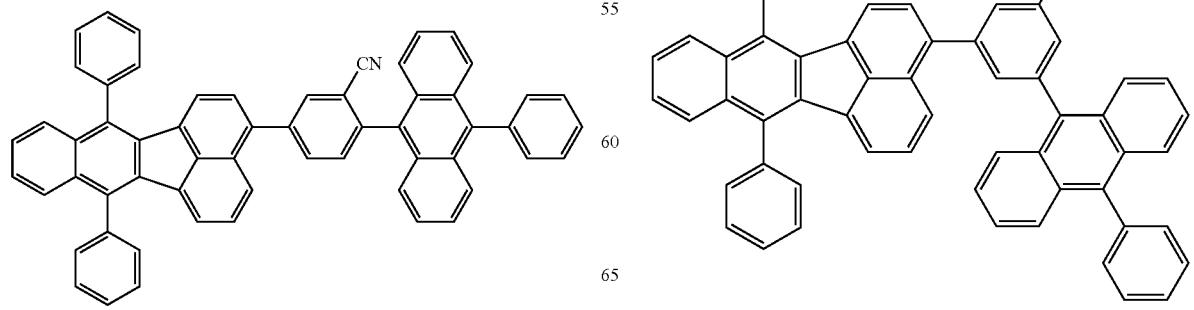

compound 10
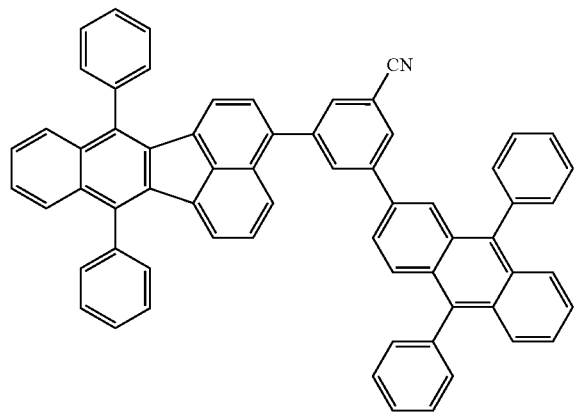
compound 12
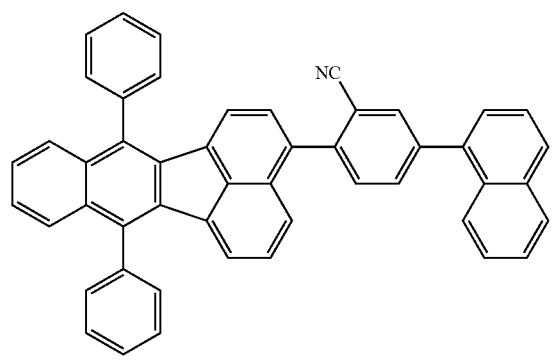
compound 12
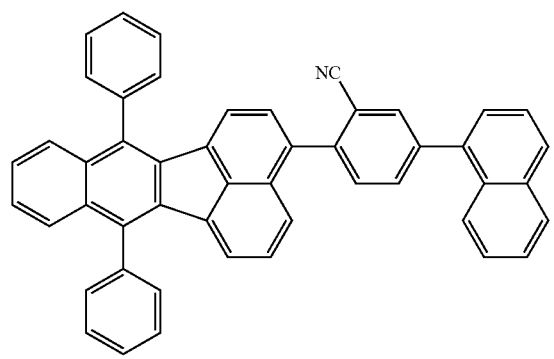
compound 13
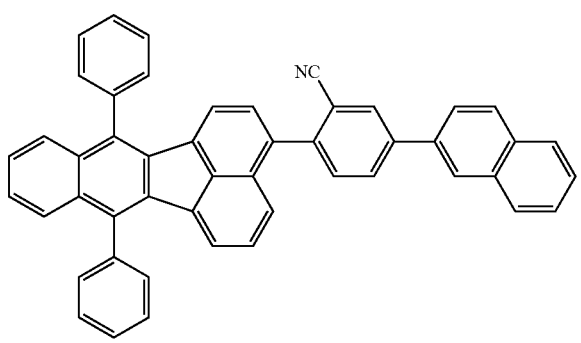
compound 14
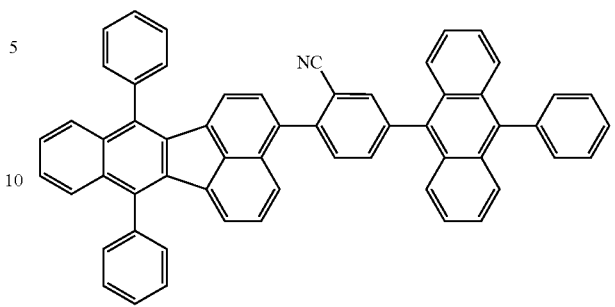
compound 15
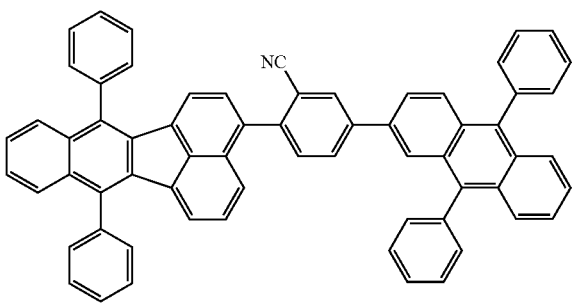
compound 16
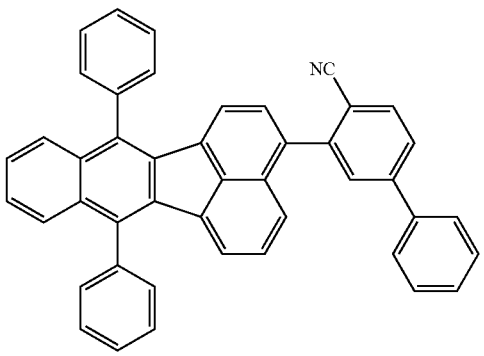
compound 17
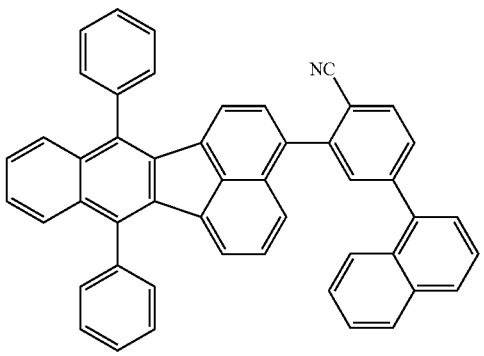

compound 18
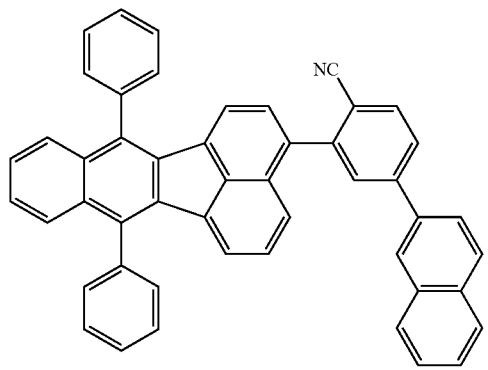
compound 19
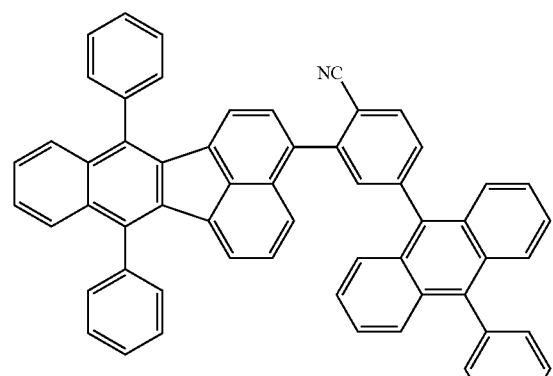
compound 20
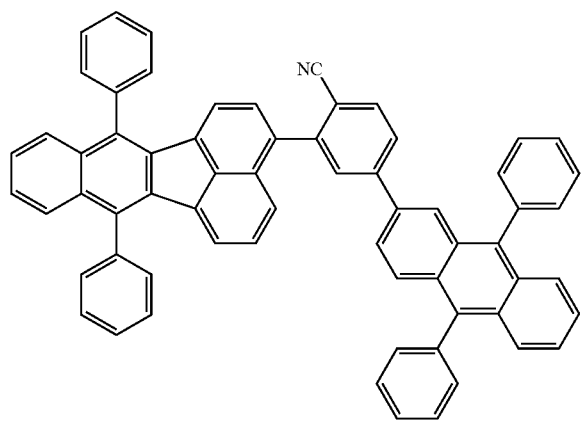
compound 22
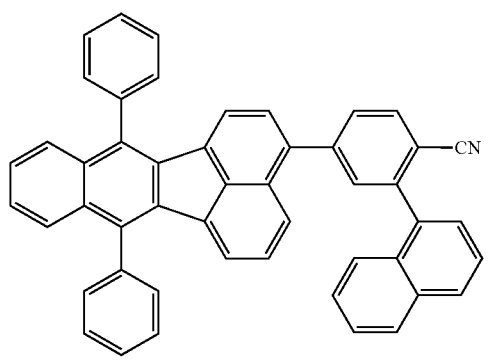
compound 23
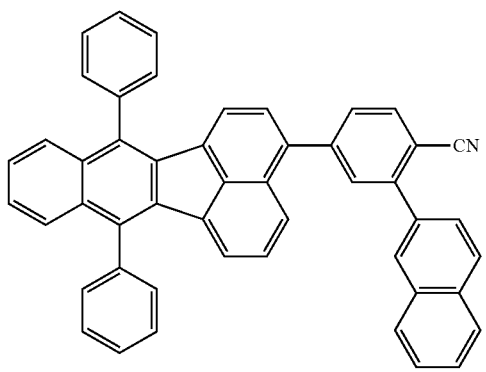
compound 24
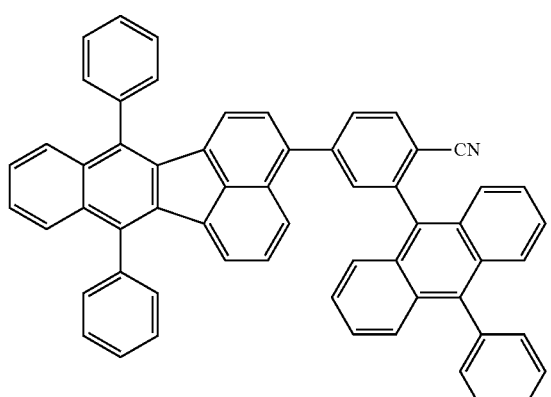
compound 24
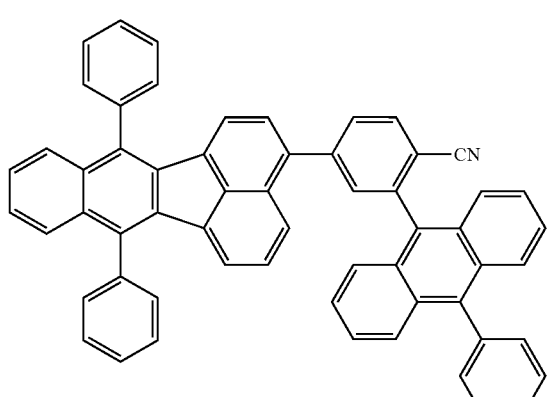

-continued compound 25

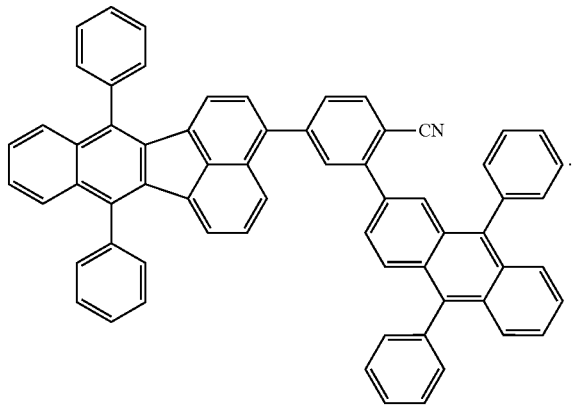

2. An organic light emitting diode, comprising:
a first electrode;
a second electrode facing the first electrode; and
a first emitting material layer positioned between the first electrode and the second electrode and including a first host and an organic emitting compound,
wherein the organic emitting compound is represented by Formula:

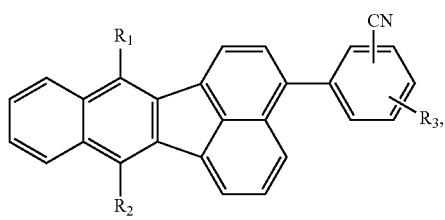

wherein each of $R_1$ and $R_2$ is independently selected from the group consisting of hydrogen, C1 to C20 alkyl group, C1 to C20 alkoxy group, C1 to C20 silyl group, C6 to C30 aryl group, C5 to C30 heteroaryl group, and amine group, and $R_3$ is selected from the group consisting of C1 to C20 alkyl group, C1 to C20 alkoxy group, C1 to C20 silyl group, C6 to C19 aryl group, C5 to C30 heteroaryl group, and amine group.

3. The organic light emitting diode according to claim 2, wherein the organic emitting compound is used as a first fluorescent dopant, and the first emitting material layer further includes a delayed fluorescent compound as a first delayed fluorescent dopant.

4. The organic light emitting diode according to claim 3, wherein a difference between an energy level of a highest occupied molecular orbital (HOMO) of the first fluorescent dopant and an energy level of a HOMO of the first delayed fluorescent dopant is equal to or less than 0.3 eV.

5. The organic light emitting diode according to claim 3, wherein an energy level of a singlet state of the first delayed fluorescent dopant is greater that an energy level of a singlet state of the first fluorescent dopant.

6. The organic light emitting diode according to claim 3, wherein an energy level of a triplet state of the first delayed fluorescent dopant is smaller than an energy level of a triplet state of the first host and greater than an energy level of a triplet state of the first fluorescent dopant.

7. The organic light emitting diode according to claim 3, further comprising:
a second emitting material layer including a second host and a second delayed fluorescent dopant, and the second emitting material layer positioned between the first emitting material layer and the first electrode.

8. The organic light emitting diode according to claim 7, further comprising:
an electron blocking layer between the first electrode and the second emitting material layer,
wherein the second host is same as a material of the electron blocking layer.

9. The organic light emitting diode according to claim 3, further comprising:
a second emitting material layer including a second host and a second fluorescent dopant, and the second emitting material layer positioned between the first emitting material layer and the first electrode.

10. The organic light emitting diode according to claim 9, further comprising:
an electron blocking layer between the first electrode and the second emitting material layer,
wherein the second host is same as a material of the electron blocking layer.

11. The organic light emitting diode according to claim 3, further comprising:
a second emitting material layer including a second host and a second delayed fluorescent dopant and positioned between the first emitting material layer and the second electrode.

12. The organic light emitting diode according to claim 11, further comprising:
a hole blocking layer between the second electrode and the second emitting material layer,
wherein the second host is same as a material of the hole blocking layer.

13. The organic light emitting diode according to claim 3, further comprising:
a second emitting material layer including a second host and a second fluorescent dopant and positioned between the first emitting material layer and the second electrode.

14. The organic light emitting diode according to claim 13, further comprising:
a hole blocking layer between the second electrode and the second emitting material layer,
wherein the second host is same as a material of the hole blocking layer.

15. The organic light emitting diode according to claim 13, further comprising:
a third emitting material layer including a third host, a third fluorescent dopant, and a second delayed fluorescent dopant and positioned between the second emitting material layer and the second electrode.

16. The organic light emitting diode according to claim 15, wherein the third fluorescent dopant is the organic emitting compound.

17. The organic light emitting diode according to claim 2, wherein the organic emitting compound is from the group consisting of:
compound 1
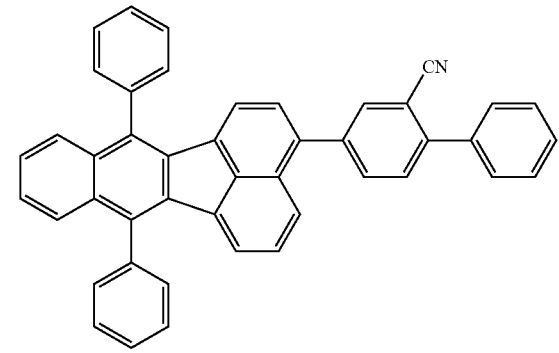
compound 2
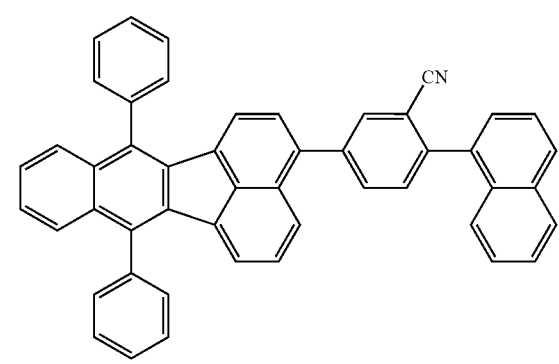
compound 3
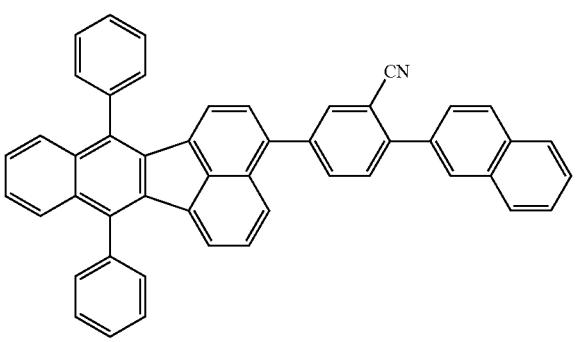
compound 4
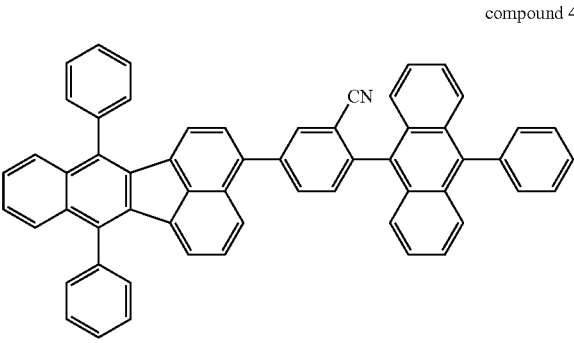
compound 5
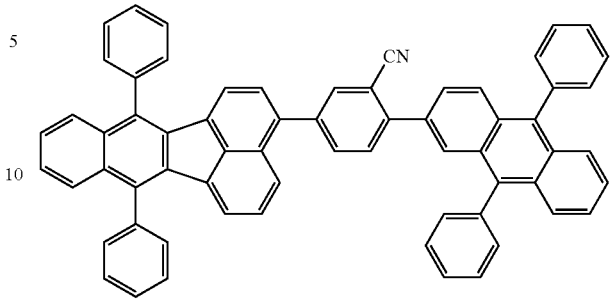
compound 6
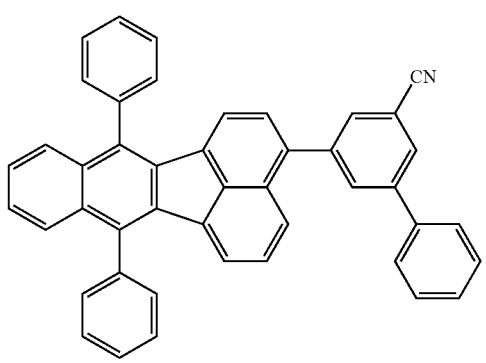
compound 7
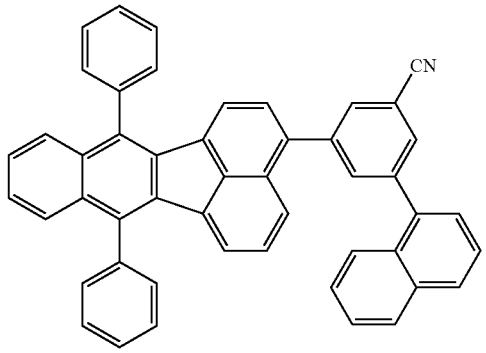
compound 8
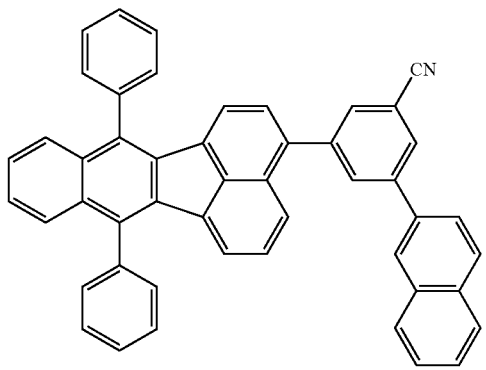

compound 9
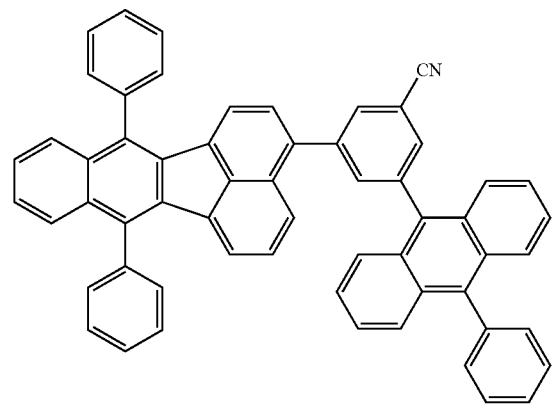
compound 10
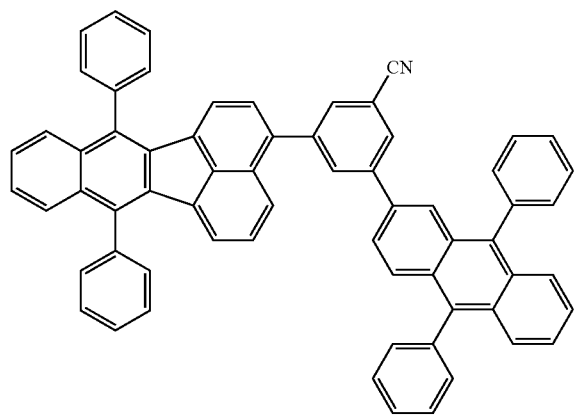
compound 11
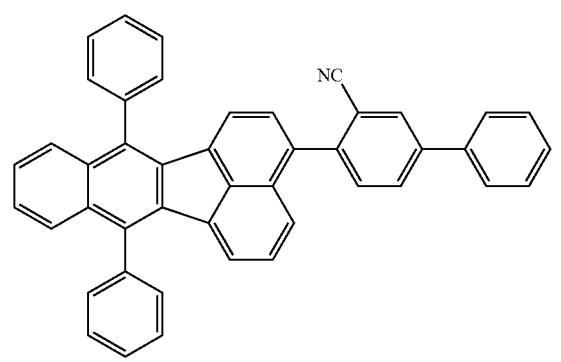
compound 12
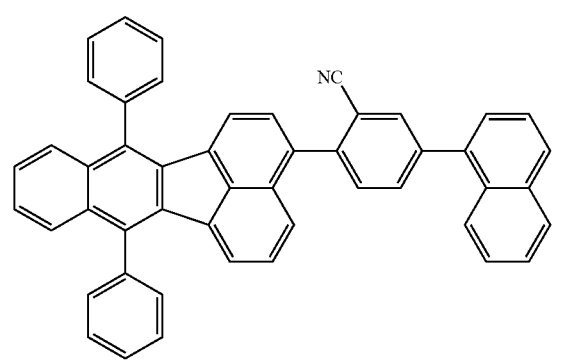
compound 13
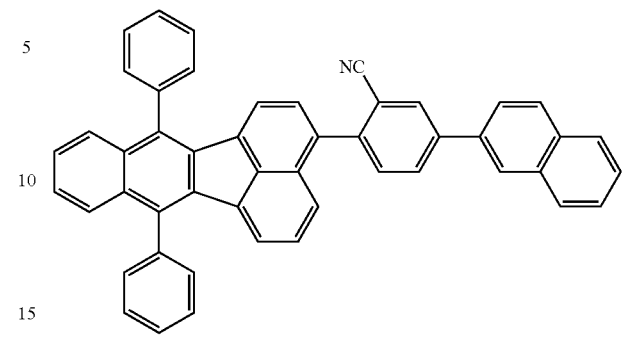
compound 14
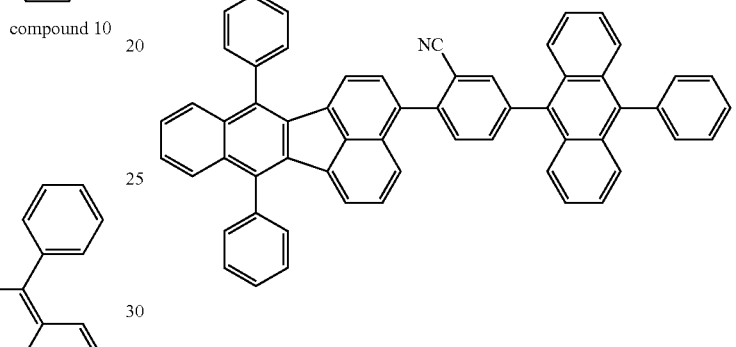
compound 15
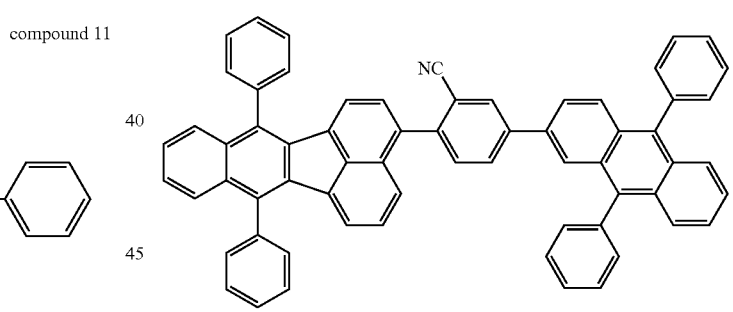
compound 16
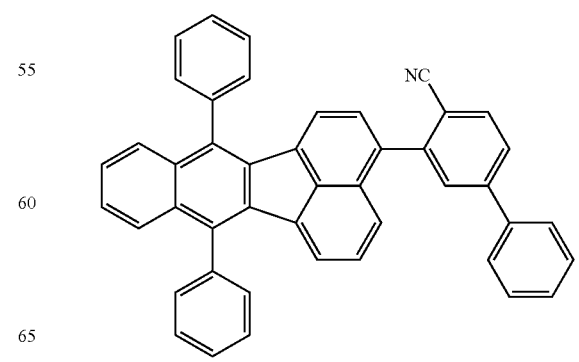

compound 17
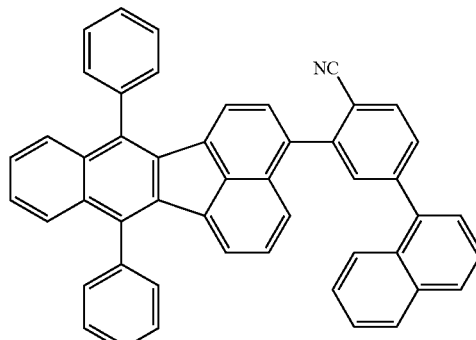
compound 18
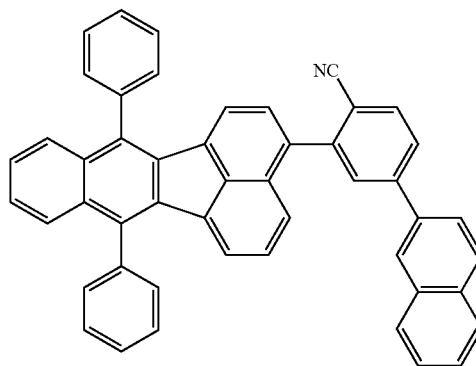
compound 19
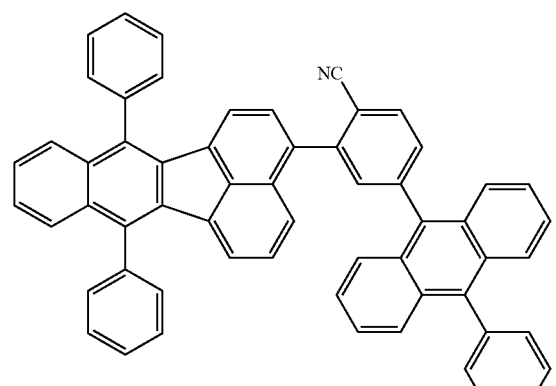
compound 20
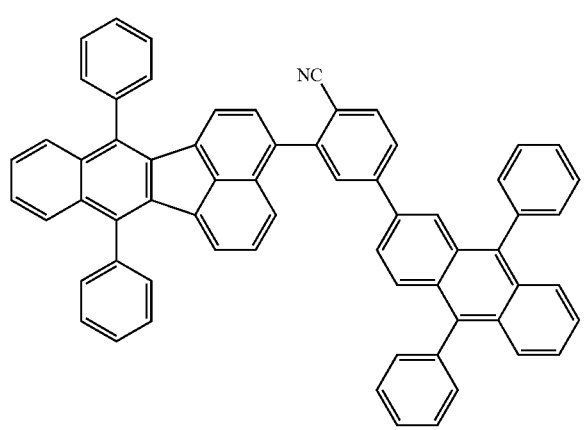
compound 21
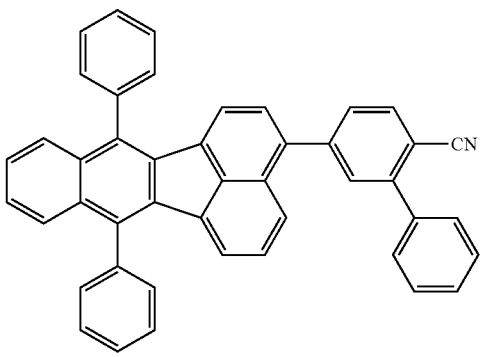
compound 22
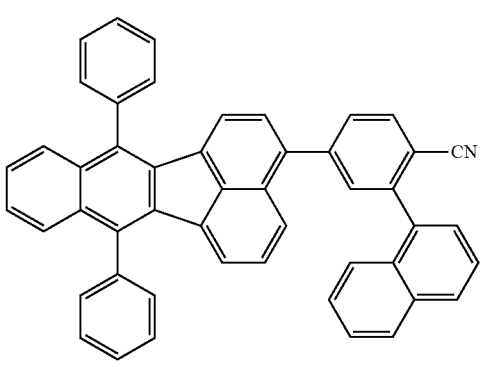
compound 23
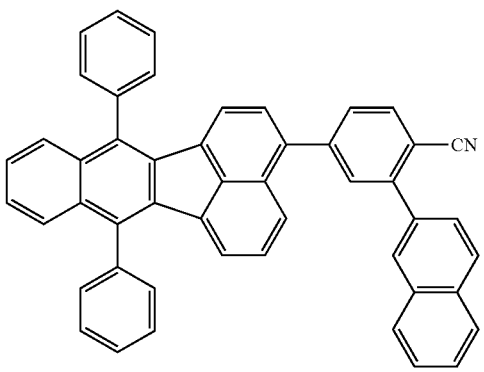
compound 24
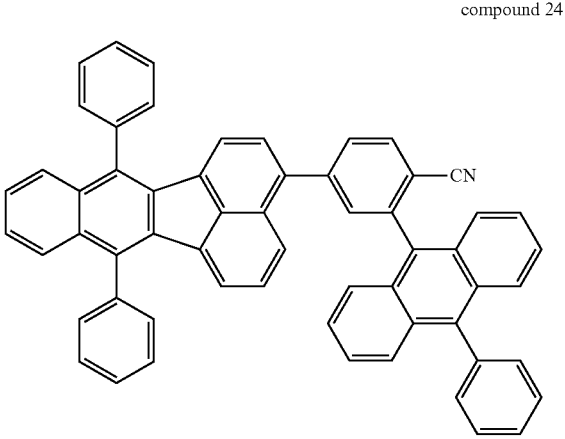

compound 25

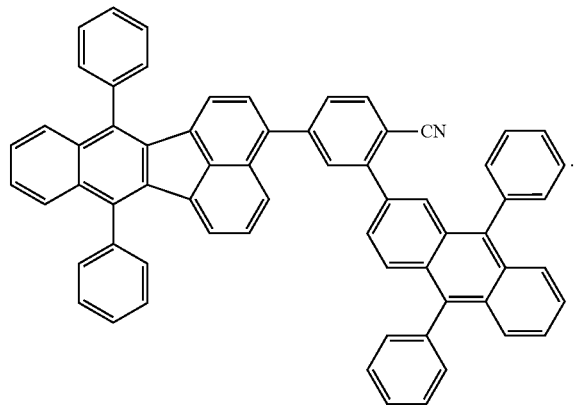

18. An organic light emitting display device, comprising:
a substrate;
an organic light emitting diode on the substrate, the organic light emitting diode including:
   a first electrode;
   a second electrode facing the first electrode; and
   a first emitting material layer positioned between the first electrode and the second electrode and including a first host and an organic emitting compound; and
an encapsulation film covering the organic light emitting diode,
wherein the organic emitting compound is from the group consisting of:

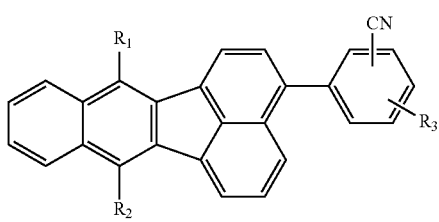

compound 1

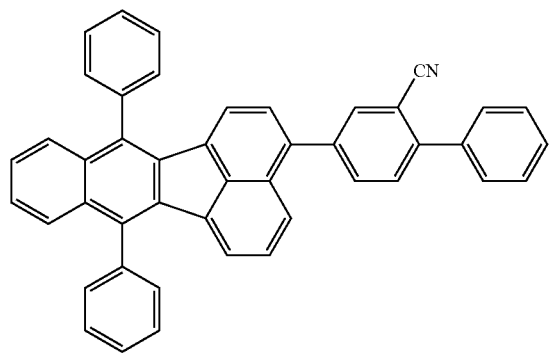

compound 2

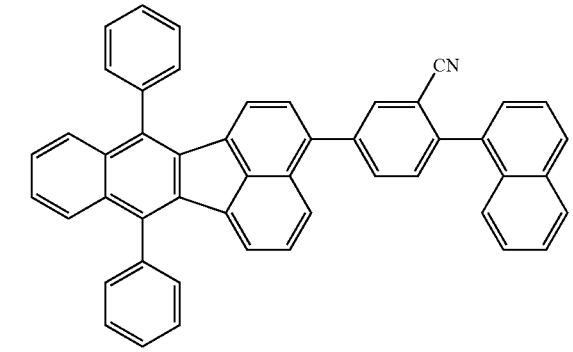

compound 3

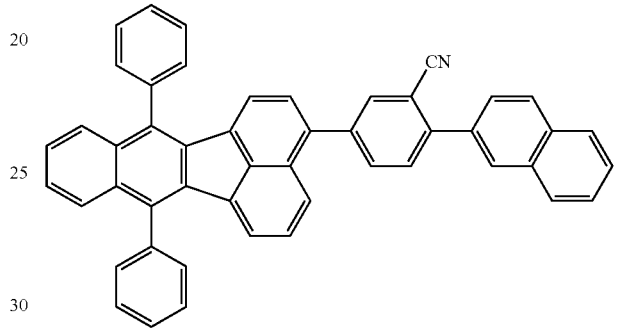

compound 4

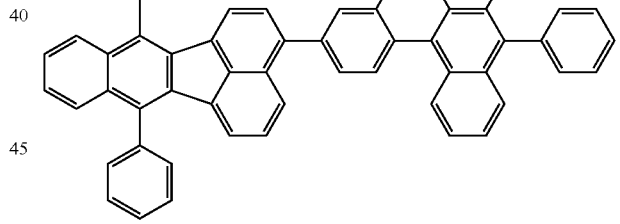

compound 5

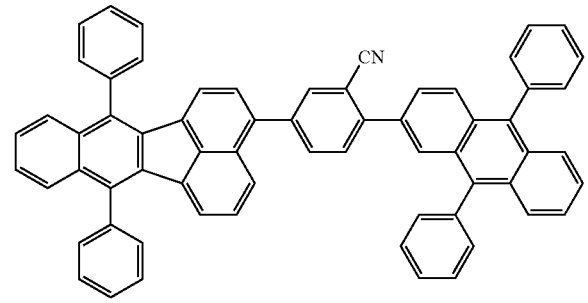

compound 6
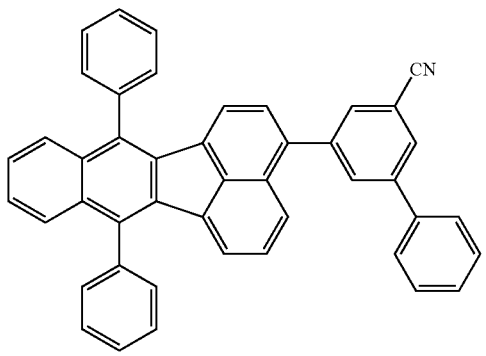
compound 7
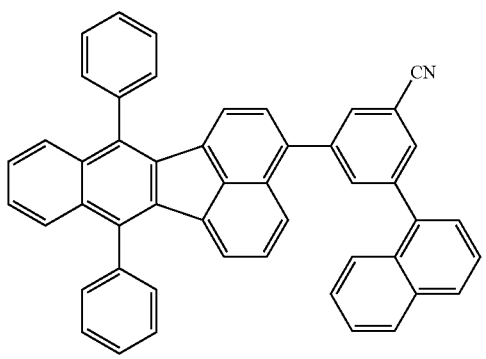
compound 8
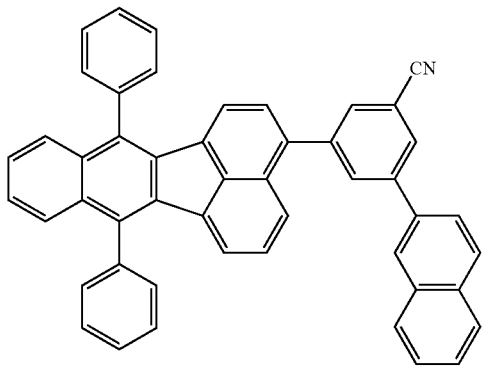
compound 9
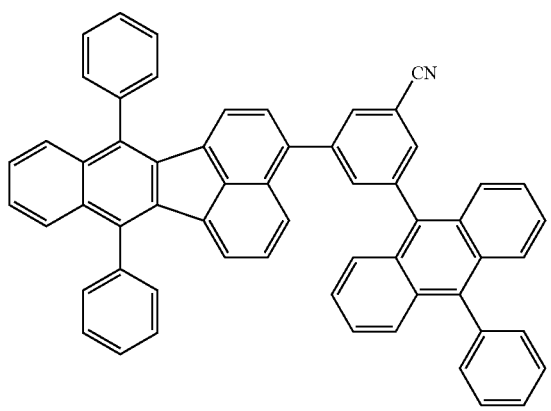
compound 10
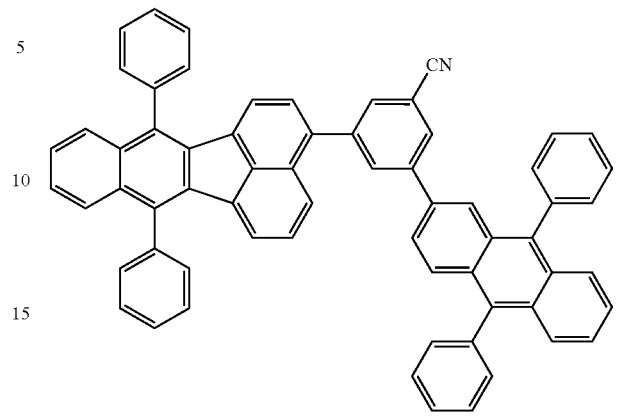
compound 11
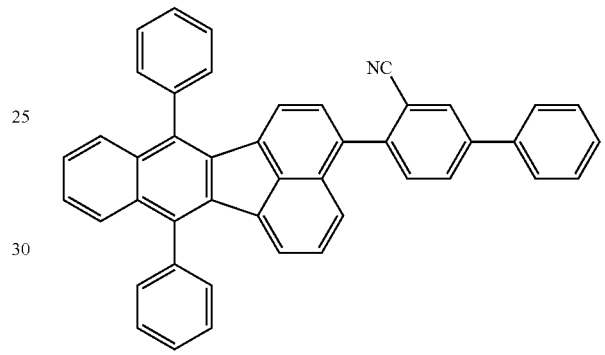
compound 12
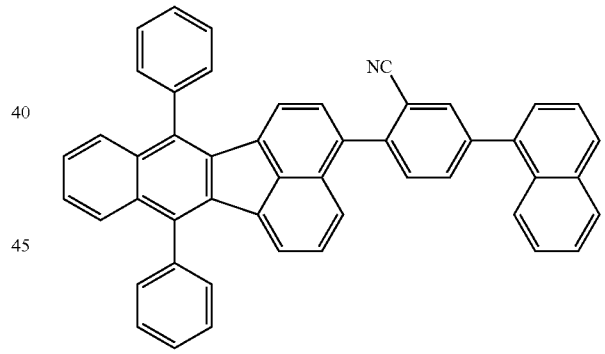
compound 13
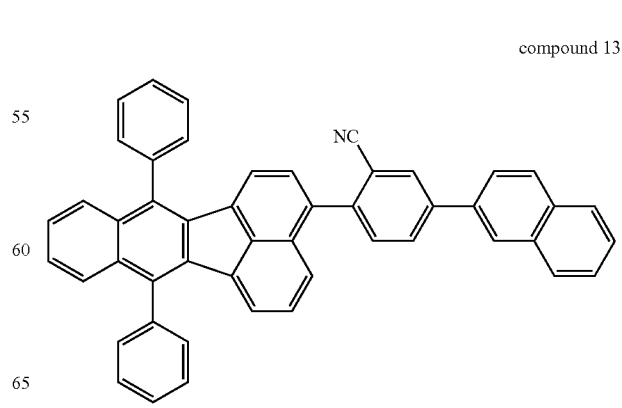

compound 14
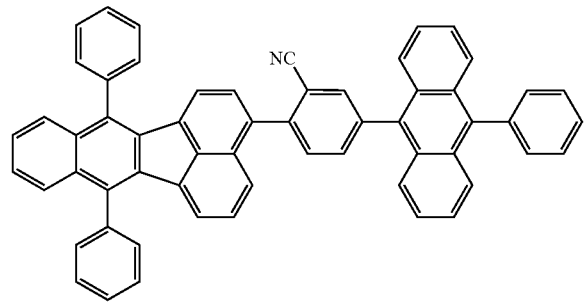
compound 15
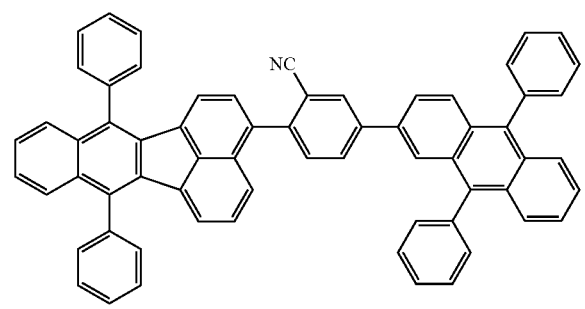
compound 16
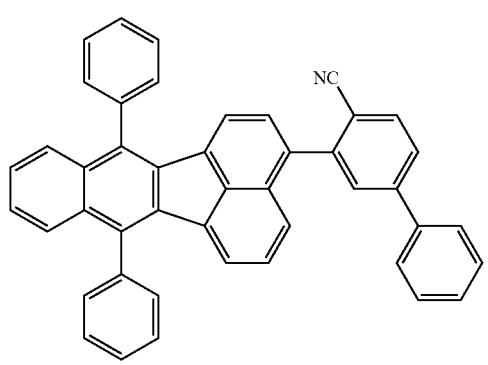
compound 17
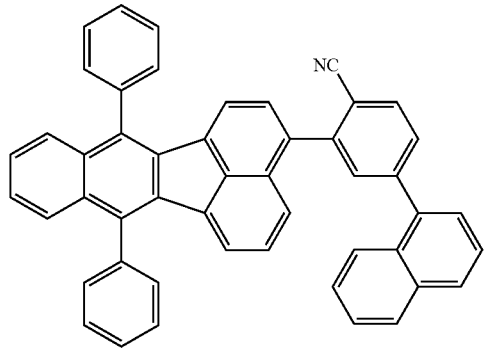
compound 18
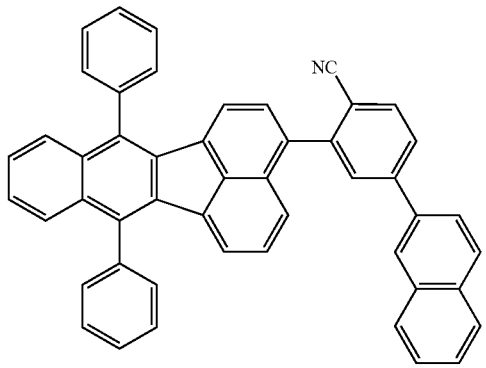
compound 19
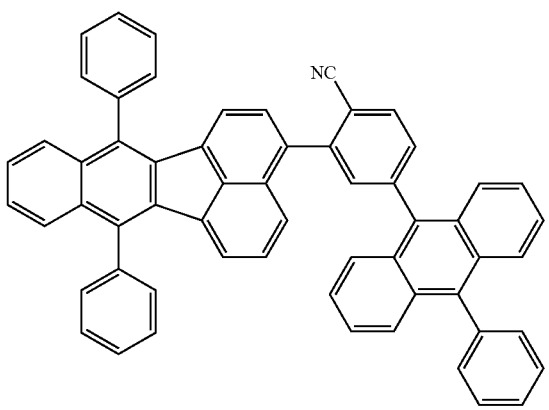
compound 20
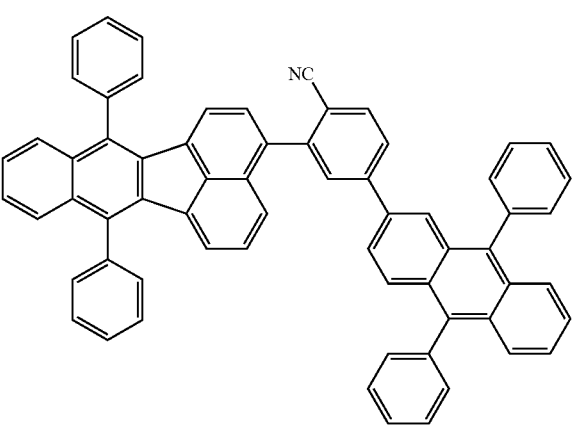

compound 21
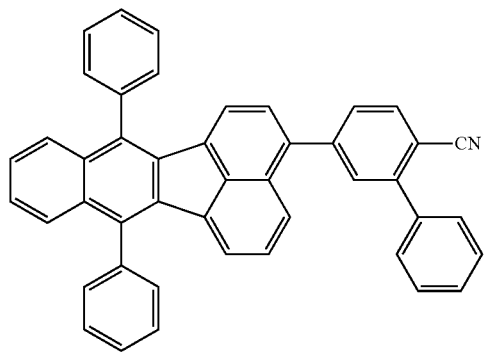
compound 22
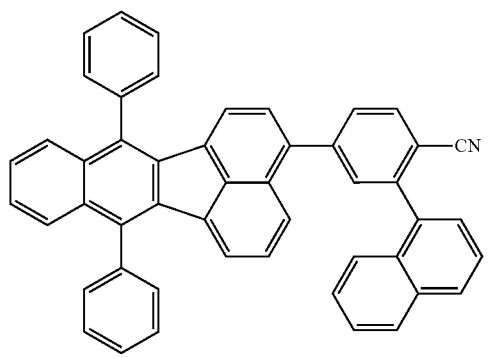
compound 23
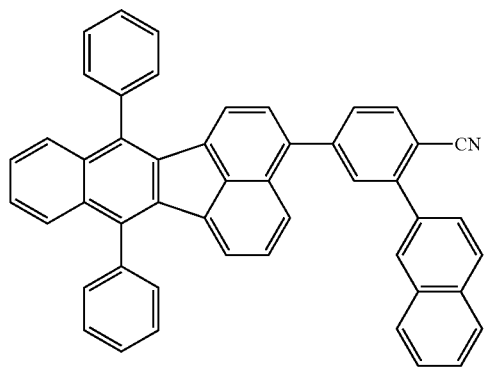
compound 24
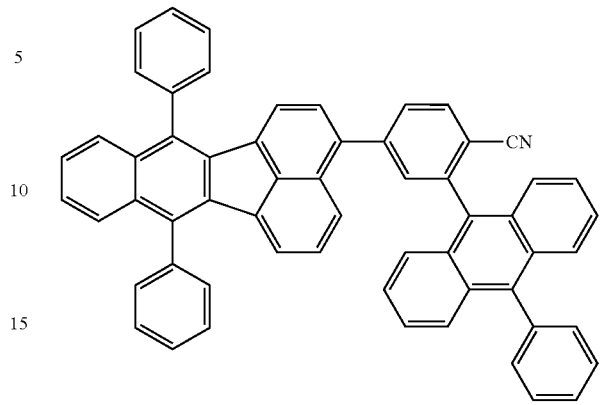
compound 25
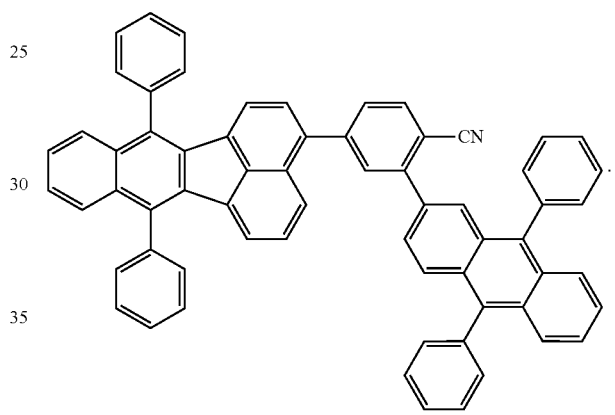
19. The organic light emitting diode according to claim 2, wherein R3 is C6 to C19 aryl group.
20. The organic light emitting display device according to claim 18, wherein R3 is C6 to C19 aryl group.
* * * * *